(12) United States Patent
Kahn et al.

(10) Patent No.: US 7,576,052 B2
(45) Date of Patent: Aug. 18, 2009

(54) METHODS AND COMPOSITIONS FOR MODULATING ADIPOCYTE FUNCTION

(75) Inventors: C. Ronald Kahn, West Newton, MA (US); Yu-Hua Tseng, Newton, MA (US); Atul Butte, Newton, MA (US)

(73) Assignees: Joslin Diabetes Center, Inc., Boston, MA (US); Children's Hospital Boston, Boston, MA (US)

( * ) Notice: Subject to any disclaimer, the term of this patent is extended or adjusted under 35 U.S.C. 154(b) by 347 days.

(21) Appl. No.: 10/968,791

(22) Filed: Oct. 18, 2004

(65) Prior Publication Data

US 2005/0187154 A1 Aug. 25, 2005

Related U.S. Application Data

(60) Provisional application No. 60/512,283, filed on Oct. 17, 2003.

(51) Int. Cl.
*A61K 38/00* (2006.01)
*A61K 38/16* (2006.01)
*A61K 38/17* (2006.01)
*A61K 38/18* (2006.01)

(52) U.S. Cl. .................. 514/2; 514/7; 514/8; 514/12

(58) Field of Classification Search ............... None
See application file for complete search history.

(56) References Cited

U.S. PATENT DOCUMENTS

| | | | | |
|---|---|---|---|---|
| 4,997,828 | A * | 3/1991 | Kappas et al. | 514/184 |
| 5,187,076 | A | 2/1993 | Wozney et al. | |
| 7,355,049 | B2 * | 4/2008 | Chu et al. | 548/202 |
| 2005/0272649 | A1 * | 12/2005 | Hruska et al. | 514/12 |

OTHER PUBLICATIONS

Asahina et al. (1996, Exp. Cell Res. 222:38-47).*
Chen et al. (2001, J. Cell. Biochem. 82:187-199).*
Science Daily, Apr. 8, 2005, "Study of Obese Diabetics Explains Why Low-carb Diets Produce Fast Results." Accessed on Apr. 28, 2008 at www.sciencedaily.com/releases/2005/050326095632.htm.*
Boden et al., "Glucocorticoid-induced differentiation of fetal rat calvarial osteoblasts is mediated by bone morphogenetic protein-6," Endocrinology 138(7):2820-8 (1997).
Celeste et al. "Identification of transforming growth factor beta family members present in bone-inductive protein purified from bovine bone," Proc. Natl. Acad. Sci. USA 87(24):9843-7 (1990).
Chen et al., "Differential roles for bone morphogenetic protein (BMP) receptor type IB and IA in differentiation and specification of mesenchymal precursor cells to osteoblast and adipocyte lineages," J. Cell Biol. 142(1):295-305 (1998).
Dernyck et al., "Human transforming growth factor-beta complementary DNA sequence and expression in normal and transformed cells," Nature 316(6030):701-5 (1985).
Einhorn, "Clinical applications of recombinant human BMPs: early experience and future development," J. Bone Joint Surg. Am. 85-A Suppl 3:82-8 (2003).

Fasshauer et al., "Essential role of insulin receptor substrate 1 in differentiation of brown adipocytes," Mol. Cell Biol. 21(1):319-29 (2001).
Gentry et al., "Molecular events in the processing of recombinant type 1 pre-pro-transforming growth factor beta to the mature polypeptide," Mol. Cell Biol. 8(10):4162-8 (1988).
Gregoire et al., "Understanding adipocyte differentiation," Physiol. Rev. 78(3):783-809 (1998).
Hamann et al., "Characterization of insulin resistance and NIDDM in transgenic mice with reduced brown fat," Diabetes 44(11):1266-73 (1995).
Hamann et al., "Decreased brown fat markedly enhances susceptibility to diet-induced obesity, diabetes, and hyperlipidemia," Endocrinology 137(1):21-9 (1996).
Klein et al., "beta(3)-adrenergic stimulation differentially inhibits insulin signaling and decreases insulin-induced glucose uptake in brown adipocytes," J. Biol. Chem. 274(49):34795-802 (1999).
Lowell et al., "Development of obesity in transgenic mice after genetic ablation of brown adipose tissue," Nature 366(6457):740-2 (1993).
MacDougald et al., "Adipogenesis: forces that tip the scales," Trends Endocrinol. Metab. 13(1):5-11 (2002).
Paulik et al., "Thiazolidinediones inhibit alkaline phosphatase activity while increasing expression of uncoupling protein, deiodinase, and increasing mitochondrial mass in C3H10T½cells," Cell Tissue Res. 290(1):79-87 (1997).
Puigserver et al., "A cold-inducible coactivator of nuclear receptors linked to adaptive thermogeneis," Cell 92(6):829-39 (1998).
Sandhu, "Bone morphogenetic proteins and spinal surgery," Spine 28(15 Suppl):S64-73 (2003).
Tamada et al., "Molecular cloning and analysis of the 5'-flanking region of the human bone morphogenetic protein-6 (BMP-6)," Biochim. Biophys. Acta. 1395(3):247-51 (1998).
Tang et al., "Commitment of C3H10T½pluripotent stem cells to the adipocyte lineage," Proc. Natl. Acad. Sci. USA 101(26):9607-11 (2004).
Todaro and Green, "Quantitative studies of the growth of mouse embryo cells in culture and their development into established lines," J. Cell Biol. 17:299-313 (1963).
Tseng et al., "Differential roles of insulin receptor substrates in the anti-apoptotic function of insulin-like growth factor-1 and insulin," J. Biol. Chem. 277(35):31601-11 (2002).
Tseng et al., "Differential roles of insulin receptor substrates in brown adipocyte differentiation," Mol. Cell Biol. 24(5):1918-29 (2004).
Wozney et al., "Novel regulators of bone formation: molecular clones and activities," Science 242(4885):1528-34 (1988).

(Continued)

*Primary Examiner*—Elizabeth C. Kemmerer
(74) *Attorney, Agent, or Firm*—Fish & Richardson P.C.

(57) ABSTRACT

Methods and compositions for treating obesity and related disorders. The methods include the use of BMP-2, -4, -6 and -7.

21 Claims, 5 Drawing Sheets

OTHER PUBLICATIONS

Klaus et al., "Functional assessment of white and brown adipocyte development and energy metabolism in cell culture. Dissociation of terminal differentiation and thermogenesis in brown adipocytes," J. Cell. Sci. 108:3171-3180 (1995).

UniProtKB Entry: P12644; Entry Name BMP4_HUMAN; Integrated into Swiss-Prot on Oct. 1, 1989.

UniProtKB Entry: P18075; Entry Name BMP7_HUMAN; Integrated into Swiss-Prot on Nov. 1, 1990.

UniProtKB Entry: P22003; Entry Name BMP5_HUMAN; Integrated into Swiss-Prot on Aug. 1, 1991.

UniProtKB Entry: P22004; Entry Name BMP6_HUMAN; Integrated into Swiss-Prot on Aug. 1, 1991.

UniProtKB Entry: P12643; Entry Name BMP2_HUMAN; Integrated into Swiss-Prot on Oct. 1, 1989.

Zhou et al., Cidea-deficient mice have lean phenotype and are resistant to obesity. Nature Genetics, 35:49-56, 2003.

Tvrdik et al., Cig30, a mouse member of a novel membrane protein gene family, is involved in the recruitment of brown adipose tissue. Jour. Biol. Chem., 272:31738 31746, 1997.

Leonard et al., Thyroxine 5'-deiodinase activity in brown adipose tissue. Endocrinology, 112:1153-1155, 1983, Abstract.

\* cited by examiner

SEQUENCE LISTING

<160> NUMBER OF SEQ ID NOS: 5

<210> SEQ ID NO 1
<211> LENGTH: 396
<212> TYPE: PRT
<213> ORGANISM: Homo sapiens

<400> SEQUENCE: 1

```
Met Val Ala Gly Thr Arg Cys Leu Leu Ala Leu Leu Leu Pro Gln Val
 1               5                  10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
            35                  40                  45

Val Leu Ser Glu Phe Glu Leu Arg Leu Leu Ser Met Phe Gly Leu Lys
50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
                100                 105                 110

His His Glu Glu Ser Leu Glu Glu Leu Pro Glu Thr Ser Gly Lys Thr
            115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
                180                 185                 190

Asp Thr Arg Leu Val Asn Gln Asn Ala Ser Arg Trp Glu Ser Phe Asp
            195                 200                 205

Val Thr Pro Ala Val Met Arg Trp Thr Ala Gln Gly His Ala Asn His
            210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
                260                 265                 270

Gly His Pro Leu His Lys Arg Glu Lys Arg Gln Ala Lys His Lys Gln
            275                 280                 285

Arg Lys Arg Leu Lys Ser Ser Cys Lys Arg His Pro Leu Tyr Val Asp
290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
            355                 360                 365

Ile Ser Met Leu Tyr Leu Asp Glu Asn Glu Lys Val Val Leu Lys Asn
370                 375                 380

Tyr Gln Asp Met Val Val Glu Gly Cys Gly Cys Arg
385                 390                 395

<210> SEQ ID NO 2
<211> LENGTH: 408
```

```
<212> TYPE: PRT
<213> ORGANISM: Homo sapiens

<400> SEQUENCE: 2

Met Ile Pro Gly Asn Arg Met Leu Met Val Leu Leu Cys Gln Val
 1               5                  10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
    130                 135                 140

Ser Ser Ile Pro Glu Asn Glu Ala Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn
        195                 200                 205

Val Thr Arg Trp Glu Thr Phe Asp Val Ser Pro Ala Val Leu Arg Trp
    210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
        275                 280                 285

Arg Ala Lys Arg Ser Pro Lys His His Ser Gln Arg Ala Arg Lys Lys
    290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
        355                 360                 365

Pro Lys Ala Cys Cys Val Pro Thr Glu Leu Ser Ala Ile Ser Met Leu
    370                 375                 380

Tyr Leu Asp Glu Tyr Asp Lys Val Val Leu Lys Asn Tyr Gln Glu Met
385                 390                 395                 400
```

Val Val Glu Gly Cys Gly Cys Arg
                405

<210> SEQ ID NO 3
<211> LENGTH: 454
<212> TYPE: PRT
<213> ORGANISM: Homo sapiens

<400> SEQUENCE: 3

Met His Leu Thr Val Phe Leu Leu Lys Gly Ile Val Gly Phe Leu Trp
 1               5                  10                  15

Ser Cys Trp Val Leu Val Gly Tyr Ala Lys Gly Gly Leu Gly Asp Asn
             20                  25                  30

His Val His Ser Ser Phe Ile Tyr Arg Arg Leu Arg Asn His Glu Arg
         35                  40                  45

Arg Glu Ile Gln Arg Glu Ile Leu Ser Ile Leu Gly Leu Pro His Arg
     50                  55                  60

Pro Arg Pro Phe Ser Pro Gly Lys Gln Ala Ser Ser Ala Pro Leu Phe
 65                  70                  75                  80

Met Leu Asp Leu Tyr Asn Ala Met Thr Asn Glu Glu Asn Pro Glu Glu
                 85                  90                  95

Ser Glu Tyr Ser Val Arg Ala Ser Leu Ala Glu Glu Thr Arg Gly Ala
            100                 105                 110

Arg Lys Gly Tyr Pro Ala Ser Pro Asn Gly Tyr Pro Arg Arg Ile Gln
        115                 120                 125

Leu Ser Arg Thr Thr Pro Leu Thr Thr Gln Ser Pro Pro Leu Ala Ser
    130                 135                 140

Leu His Asp Thr Asn Phe Leu Asn Asp Ala Asp Met Val Met Ser Phe
145                 150                 155                 160

Val Asn Leu Val Glu Arg Asp Lys Asp Phe Ser His Gln Arg Arg His
                165                 170                 175

Tyr Lys Glu Phe Arg Phe Asp Leu Thr Gln Ile Pro His Gly Glu Ala
            180                 185                 190

Val Thr Ala Ala Glu Phe Arg Ile Tyr Lys Asp Arg Ser Asn Asn Arg
        195                 200                 205

Phe Glu Asn Glu Thr Ile Lys Ile Ser Ile Tyr Gln Ile Ile Lys Glu
    210                 215                 220

Tyr Thr Asn Arg Asp Ala Asp Leu Phe Leu Leu Asp Thr Arg Lys Ala
225                 230                 235                 240

Gln Ala Leu Asp Val Gly Trp Leu Val Phe Asp Ile Thr Val Thr Ser
                245                 250                 255

Asn His Trp Val Ile Asn Pro Gln Asn Asn Leu Gly Leu Gln Leu Cys
            260                 265                 270

Ala Glu Thr Gly Asp Gly Arg Ser Ile Asn Val Lys Ser Ala Gly Leu
        275                 280                 285

Val Gly Arg Gln Gly Pro Gln Ser Lys Gln Pro Phe Met Val Ala Phe
    290                 295                 300

Phe Lys Ala Ser Glu Val Leu Leu Arg Ser Val Arg Ala Ala Asn Lys
305                 310                 315                 320

Arg Lys Asn Gln Asn Arg Asn Lys Ser Ser His Gln Asp Ser Ser
                325                 330                 335

Arg Met Ser Ser Val Gly Asp Tyr Asn Thr Ser Glu Gln Lys Gln Ala
            340                 345                 350

Cys Lys Lys His Glu Leu Tyr Val Ser Phe Arg Asp Leu Gly Trp Gln

-continued

```
                355                 360                 365
Asp Trp Ile Ile Ala Pro Glu Gly Tyr Ala Ala Phe Tyr Cys Asp Gly
    370                 375                 380

Glu Cys Ser Phe Pro Leu Asn Ala His Met Asn Ala Thr Asn His Ala
385                 390                 395                 400

Ile Val Gln Thr Leu Val His Leu Met Phe Pro Asp His Val Pro Lys
                405                 410                 415

Pro Cys Cys Ala Pro Thr Lys Leu Asn Ala Ile Ser Val Leu Tyr Phe
            420                 425                 430

Asp Asp Ser Ser Asn Val Ile Leu Lys Lys Tyr Arg Asn Met Val Val
        435                 440                 445

Arg Ser Cys Gly Cys His
    450

<210> SEQ ID NO 4
<211> LENGTH: 513
<212> TYPE: PRT
<213> ORGANISM: Homo sapiens

<400> SEQUENCE: 4

Met Pro Gly Leu Gly Arg Arg Ala Gln Trp Leu Cys Trp Trp Trp Gly
1               5                   10                  15

Leu Leu Cys Ser Cys Cys Gly Pro Pro Leu Arg Pro Pro Leu Pro
            20                  25                  30

Ala Ala Ala Ala Ala Ala Gly Gly Gln Leu Leu Gly Asp Gly Gly
            35                  40                  45

Ser Pro Gly Arg Thr Glu Gln Pro Pro Ser Pro Gln Ser Ser Ser
    50                  55                  60

Gly Phe Leu Tyr Arg Arg Leu Lys Thr Gln Glu Lys Arg Glu Met Gln
65                  70                  75                  80

Lys Glu Ile Leu Ser Val Leu Gly Leu Pro His Arg Pro Arg Pro Leu
                85                  90                  95

His Gly Leu Gln Gln Pro Gln Pro Pro Ala Leu Arg Gln Gln Glu Glu
            100                 105                 110

Gln Gln Gln Gln Gln Gln Leu Pro Arg Gly Glu Pro Pro Pro Gly Arg
        115                 120                 125

Leu Lys Ser Ala Pro Leu Phe Met Leu Asp Leu Tyr Asn Ala Leu Ser
    130                 135                 140

Ala Asp Asn Asp Glu Asp Gly Ala Ser Glu Gly Glu Arg Gln Gln Ser
145                 150                 155                 160

Trp Pro His Glu Ala Ala Ser Ser Ser Gln Arg Arg Gln Pro Pro Pro
                165                 170                 175

Gly Ala Ala His Pro Leu Asn Arg Lys Ser Leu Leu Ala Pro Gly Ser
            180                 185                 190

Gly Ser Gly Gly Ala Ser Pro Leu Thr Ser Ala Gln Asp Ser Ala Phe
        195                 200                 205

Leu Asn Asp Ala Asp Met Val Met Ser Phe Val Asn Leu Val Glu Tyr
    210                 215                 220

Asp Lys Glu Phe Ser Pro Arg Gln Arg His His Lys Glu Phe Lys Phe
225                 230                 235                 240

Asn Leu Ser Gln Ile Pro Glu Gly Glu Val Val Thr Ala Ala Glu Phe
                245                 250                 255

Arg Ile Tyr Lys Asp Cys Val Met Gly Ser Phe Lys Asn Gln Thr Phe
            260                 265                 270
```

```
Leu Ile Ser Ile Tyr Gln Val Leu Gln Glu His Gln His Arg Asp Ser
        275                 280                 285

Asp Leu Phe Leu Leu Asp Thr Arg Val Val Trp Ala Ser Glu Glu Gly
        290                 295                 300

Trp Leu Glu Phe Asp Ile Thr Ala Thr Ser Asn Leu Trp Val Val Thr
305                 310                 315                 320

Pro Gln His Asn Met Gly Leu Gln Leu Ser Val Val Thr Arg Asp Gly
                    325                 330                 335

Val His Val His Pro Arg Ala Ala Gly Leu Val Gly Arg Asp Gly Pro
                340                 345                 350

Tyr Asp Lys Gln Pro Phe Met Val Ala Phe Lys Val Ser Glu Val
                355                 360                 365

His Val Arg Thr Thr Arg Ser Ala Ser Ser Arg Arg Gln Gln Ser
                370                 375                 380

Arg Asn Arg Ser Thr Gln Ser Gln Asp Val Ala Arg Val Ser Ser Ala
385                 390                 395                 400

Ser Asp Tyr Asn Ser Ser Glu Leu Lys Thr Ala Cys Arg Lys His Glu
                    405                 410                 415

Leu Tyr Val Ser Phe Gln Asp Leu Gly Trp Gln Asp Trp Ile Ile Ala
                420                 425                 430

Pro Lys Gly Tyr Ala Ala Asn Tyr Cys Asp Gly Glu Cys Ser Phe Pro
                435                 440                 445

Leu Asn Ala His Met Asn Ala Thr Asn His Ala Ile Val Gln Thr Leu
                450                 455                 460

Val His Leu Met Asn Pro Glu Tyr Val Pro Lys Pro Cys Cys Ala Pro
465                 470                 475                 480

Thr Lys Leu Asn Ala Ile Ser Val Leu Tyr Phe Asp Asp Asn Ser Asn
                    485                 490                 495

Val Ile Leu Lys Lys Tyr Arg Asn Met Val Val Arg Ala Cys Gly Cys
                500                 505                 510

His
```

<210> SEQ ID NO 5
<211> LENGTH: 431
<212> TYPE: PRT
<213> ORGANISM: Homo sapiens

<400> SEQUENCE: 5

```
Met His Val Arg Ser Leu Arg Ala Ala Ala Pro His Ser Phe Val Ala
1                   5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125
```

-continued

```
Asp Ala Asp Met Val Met Ser Phe Val Asn Leu Val Glu His Asp Lys
        130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430
```

METHODS AND COMPOSITIONS FOR MODULATING ADIPOCYTE FUNCTION

CLAIM OF PRIORITY

This application claims the benefit under 35 USC § 119(e) to U.S. Provisional Patent Application Ser. No. 60/512,283, filed on Oct. 17, 2003, the entire contents of which are hereby incorporated by reference.

FEDERALLY SPONSORED RESEARCH OR DEVELOPMENT

The U.S. Government has certain rights in this invention pursuant to Grants No. K12DK63696 and DK33201 awarded by the National Institutes of Health.

BACKGROUND

Bone morphogenetic proteins (BMPs) belong to the TGFβ superfamily. BMPs bind to specific type-I and -II serine/threonine kinase receptor complexes, RIa, RIb, and RII, which signal through SMAD proteins or the p38 mitogen-activated protein kinase (MAPK). The BMPs are important regulators of key events in many aspects of tissue development and morphogenesis, including the processes of bone formation during embryogenesis, postnatal growth, remodeling and regeneration of the skeleton. Localization studies in both human and mouse tissues have demonstrated high levels of mRNA expression and protein synthesis for various BMPs in adipose, heart, lung, small intestine, limb bud and teeth.

Several BMPs have been implicated in early skeletal development, including BMP-2, -4, -5, -7, -14 (CDMP-1/GDF-5). Other members, such as BMP-3, -6, -7 and -13 (CDMP-2/GDF-6) may be involved in later stages of skeletal formation.

SUMMARY OF THE INVENTION

The present invention is based, in part, on the discovery that bone morphogenetic proteins 2, 4, 6, and 7 (BMP-2, -4, -5, -6, and -7) play an important role in adipocyte differentiation. In particular, it has been found that BMP-2, -4, -5, -6, and -7 promote brown adipocyte tissue (BAT) differentiation and inhibits white adipose tissue (WAT) adipogenesis. Since BAT is specialized for energy expenditure and WAT is involved in energy storage, BMP-2, -4, -5, -6, and/or -7 provide a therapeutic, screening and diagnostic target for obesity and related disorders, such as diabetes.

Accordingly, in one aspect, the invention features methods of modulating adipose tissue function or development, e.g., promoting BAT differentiation and/or reducing WAT adipogenesis. The methods include modulating BMP-2, -4, -5, -6, and/or -7 signaling. In some embodiments, the methods include increasing BMP-2, -4, -5, -6, and/or -7 signaling, e.g., increasing BMP-2, -4, -5, -6, and/or -7 expression, levels, or activity, in a preadipocyte, to thereby reduce WAT adipogenesis and/or increase BAT differentiation.

In one embodiment, the methods include providing a population of brown or white preadipocyte and/or adipocyte cells (e.g., a population of cells in which at least 30%, 40%, preferably 50%, more preferably 60%, 70%, 80%, 90% or more of the cells are, preadipocyte and/or adipocyte cells); and contacting the cells with an agent that modulates, e.g., increases expression, levels or activity of one or more of BMP-2, -4, -5, -6, and/or -7.

In some embodiments, the agent is a BMP-2, -4, -5, -6, and/or -7 polypeptide or nucleic acid. As used herein a "BMP-2, -4, -5, -6, and/or -7 polypeptide or nucleic acid" is a BMP-2, -4, -5, -6, and/or -7 polypeptide or nucleic acid as described herein, e.g., a mature human BMP-2, -4, -5, -6, and/or -7 polypeptide or active fragment thereof, or a nucleic acid encoding a mature human BMP-2, -4, -5, -6, and/or -7 polypeptide or active fragment thereof.

In one embodiment, the agent is a BMP-2 polypeptide, preferably human, preferably a mature BMP-2 polypeptide, e.g., a BMP-2 polypeptide that includes amino acids 283-396 of SEQ ID NO:1. The polypeptide can be a recombinant polypeptide.

In one embodiment, the agent is a BMP-4 polypeptide, preferably human, preferably a mature BMP-4 polypeptide, e.g., a BMP-4 polypeptide that includes amino acids 293-408 of SEQ ID NO:2. The polypeptide can be a recombinant polypeptide.

In one embodiment, the agent is a BMP-5 polypeptide, preferably human, preferably a mature BMP-5 polypeptide, e.g., a BMP-4 polypeptide that includes amino acids 323-454 of SEQ ID NO:3. The polypeptide can be a recombinant polypeptide.

In one embodiment, the agent is a BMP-6 polypeptide, preferably human, preferably a mature BMP-6 polypeptide, e.g., a BMP-6 polypeptide that includes amino acids 374-513 of SEQ ID NO:4, amino acids 382-513 of SEQ ID NO:4, amino acids 388-513 of SEQ ID NO:4, or amino acids 412-513 of SEQ ID NO:4. The polypeptide can be a recombinant polypeptide.

In one embodiment, the agent is a BMP-7 polypeptide, preferably human, preferably a mature BMP-7 polypeptide, e.g., a BMP-7 polypeptide that includes amino acids 293-431 of SEQ ID NO:5. The polypeptide can be a recombinant polypeptide.

In some embodiments, the methods include contacting, administering or expressing one or more other compounds in addition to the BMP, e.g., PPARγ, Retinoid X receptor, alpha (RxRa), insulin, T3, a thiazolidinedione (TZD), retinoic acid, or other compound.

The methods can be performed in vitro or in vivo. For the example, the methods can include contacting cultured preadipocytes or adipocyte with the agent in an amount sufficient to increase BAT differentiation or inhibit WAT. In one embodiment, the method further includes implanting the cell or cell population in a subject. In some embodiments, the cells are in a subject, e.g., a human subject, e.g., an obese human subject.

In some embodiments, the methods include evaluating the level of BAT differentiation in the cell or cell population. BAT differentiation can be evaluated by measuring any of, e.g., a BAT marker, such as uncoupling protein (UCP), e.g., UCP-1, expression; BAT morphology (e.g., using visual, e.g., microscopic, inspection of the cells); or BAT thermodynamics, e.g., cytochrome oxidase activity, Na+-K+-ATPase enzyme units, or other enzymes involved in BAT thermogenesis. In other embodiments, the methods include evaluating WAT differentiation, e.g., evaluating a WAT specific marker or WAT morphology.

In one embodiment, the BMP-2, -4, -5, -6, and/or -7 is administered in combination with another agent, e.g., another BMP protein (e.g., BMP-1 or BMP-3), vitamin A, retinoic acid, insulin, glucocorticoid or agonist thereof, Wnt, IGF, or other growth factor, e.g., EGF, FGF, TGFα, TGFβ, TNFα, MCSF, VEGF and/or PDFG. In other embodiments, the agent can be a BMP-2, -4, -5, -6, and/or -7 protein as described herein or a portion thereof linked with a heterologous polypeptide sequence, e.g., a second BMP protein, to form a chimeric molecule or fusion protein.

In some embodiments, the BMP-2, -4, -5, -6, and/or -7 polypeptide is exogenously added to the cell or cell population. In other embodiments, a cell genetically engineered to express (e.g., overexpress) BMP-2, -4, -5, -6, and/or -7 is co-cultured with the cell or cell population.

An agent that increases BMP-2, -4, -5, -6, and/or -7 signaling, to thereby reduce WAT adipogenesis and/or increase BAT differentiation can be, e.g., (a) a BMP-2, -4, -5, -6, and/or -7 polypeptide or a functional fragment or variant thereof, preferably an active (e.g., BMPR-I and/or BMPR-II activating) BMP-2, -4, -5, -6, and/or -7 polypeptide or a functional fragment or analog thereof (e.g., a mature BMP-2, -4, -5, -6, and/or -7 polypeptide, e.g., a mature BMP-2, -4, -5, -6, and/or -7 polypeptide described herein); (b) a peptide or protein agonist of BMP-2, -4, -5, -6, and/or -7 that increases the activity, e.g., the BMPR-I and/or BMPR-II activating activity of BMP-2, -4, -5, -6, and/or -7 (e.g., by increasing or stabilizing binding of BMP-2, -4, -5, -6, and/or -7 to its receptor); (c) a small molecule or protein mimetic that mimics BMP-2, -4, -5, -6, and/or -7 signaling activity, e.g., BMPR-I and/or BMPR-II binding activity, or SMAD phosphorylating activity; (d) a small molecule that increases expression of BMP-2, -4, -5, -6, and/or -7, e.g., by binding to the promoter region of a BMP-2, -4, -5, -6, and/or -7 gene; (e) an antibody, e.g., an antibody that binds to and stabilizes or assists the binding of BMP-2, -4, -5, -6, and/or -7 to a BMP-2, -4, -5, -6, and/or -7 binding partner (e.g., a BMP-2, -4, -5, -6, and/or -7 receptor described herein); or (f) a nucleotide sequence encoding a BMP-2, -4, -5, -6, and/or -7 polypeptide or functional fragment or analog thereof. The nucleotide sequence can be a genomic sequence or a cDNA sequence. The nucleotide sequence can include: a BMP-2, -4, -5, -6, and/or -7 coding region; a promoter sequence, e.g., a promoter sequence from a BMP-2, -4, -5, -6, and/or -7 gene or from another gene; an enhancer sequence; untranslated regulatory sequences, e.g., a 5' untranslated region (UTR), e.g., a 5'UTR from a BMP-2, -4, -5, -6, and/or -7 gene or from another gene, a 3' UTR, e.g., a 3'UTR from a BMP-2, -4, -5, -6, and/or -7 gene or from another gene; a polyadenylation site; an insulator sequence. In another embodiment, the level of BMP-2, -4, -5, -6, and/or -7 protein is increased by increasing the level of expression of an endogenous BMP-2, -4, -5, -6, and/or -7 gene, e.g., by increasing transcription of the BMP-2, -4, -5, -6, and/or -7 gene or increasing BMP-2, -4, -5, -6, and/or -7 mRNA stability. In some embodiments, transcription of the BMP-2, -4, -5, -6, and/or -7 gene is increased by: altering the regulatory sequence of the endogenous BMP-2, -4, -5, -6, and/or -7 gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the BMP-2, -4, -5, -6, and/or -7 gene to be transcribed more efficiently.

An agent that decreases BMP-2, -4, -5, -6, and/or -7 signaling to thereby increase WAT adipogenesis or decrease BAT differentiation can be, for example: a BMP-2, -4, -5, -6, and/or -7 binding protein, e.g., a soluble binding protein that binds BMP-2, -4, -5, -6, and/or -7 and inhibits a BMP-2, -4, -5, -6, and/or -7 activity, or inhibits the ability of a BMP-2, -4, -5, -6, and/or -7 to interact with a binding partner; an antibody that specifically binds to the BMP-2, -4, -5, -6, and/or -7 protein, e.g., an antibody that disrupts a the ability of BMP-2, -4, -5, -6, and/or -7 to bind to a binding partner; a mutated inactive BMP-2, -4, -5, -6, and/or -7 or fragment thereof which disrupts a BMP-2, -4, -5, -6, and/or -7 activity (e.g., a dominant negative BMP-2, -4, -5, -6, and/or -7 mutant); a BMP-2, -4, -5, -6, and/or -7 nucleic acid molecule that can bind to a cellular BMP-2, -4, -5, -6, and/or -7 nucleic acid sequence, e.g., mRNA, and inhibit expression of the protein, e.g., an antisense, siRNA molecule or BMP-2, -4, -5, -6, and/or -7 ribozyme; an agent which decreases BMP-2, -4, -5, -6, and/or -7 gene expression, e.g., a small molecule which binds and inhibits the promoter of BMP-2, -4, -5, -6, and/or -7. In another embodiment, BMP-2, -4, -5, -6, and/or -7 is inhibited by decreasing the level of expression of an endogenous BMP-2, -4, -5, -6, and/or -7 gene, e.g., by decreasing transcription of the BMP-2, -4, -5, -6, and/or -7 gene. In one embodiment, transcription of the BMP-2, -4, -5, -6, and/or -7 gene can be decreased by: altering the regulatory sequences of the endogenous BMP-2, -4, -5, -6, and/or -7 gene, e.g., by the addition of a negative regulatory sequence (such as a DNA-biding site for a transcriptional repressor), or by the removal of a positive regulatory sequence (such as an enhancer or a DNA-binding site for a transcriptional activator). In another embodiment, the antibody which binds the BMP-2, -4, -5, -6, and/or -7 is a monoclonal antibody, e.g., a humanized chimeric or human monoclonal antibody.

In another aspect, the invention features methods of treating a subject, e.g., decreasing fat stores or weight in a subject such as a human. The methods include: identifying a subject in need of decreasing fat stores or weight, and administering to the subject an agent that increases BMP-2, -4, -5, -6, and/or -7 signaling (e.g., increases BMP-2, -4, -5, -6, and/or -7 expression, levels or activity).

In one embodiment, the methods include administering a BMP-2 polypeptide in an amount sufficient to promote BAT differentiation and/or reduce WAT adipogenesis in the subject. The BMP-2 polypeptide is preferably human, and preferably a mature BMP-2 polypeptide, e.g., a BMP-2 polypeptide that includes amino acids 283-396 of SEQ ID NO:1. The polypeptide can be a recombinant polypeptide.

In one embodiment, the methods include administering a BMP-4 polypeptide in an amount sufficient to promote BAT differentiation and/or reduce WAT adipogenesis in the subject. The BMP-4 polypeptide is preferably human, and preferably a mature BMP-4 polypeptide, e.g., a BMP-4 polypeptide that includes amino acids 293-408 of SEQ ID NO:2. The polypeptide can be a recombinant polypeptide.

In one embodiment, the methods include administering a BMP-5 polypeptide in an amount sufficient to promote BAT differentiation and/or reduce WAT adipogenesis in the subject. The BMP-5 polypeptide is preferably human, and preferably a mature BMP-5 polypeptide, e.g., a BMP-5 polypeptide that includes amino acids 323-454 of SEQ ID NO:3. The polypeptide can be a recombinant polypeptide.

In one embodiment, the methods include administering a BMP-6 polypeptide in an amount sufficient to promote BAT differentiation and/or reduce WAT adipogenesis in the subject. The BMP-6 polypeptide is preferably human, and preferably a mature BMP-6 polypeptide, e.g., a BMP-6 polypeptide that includes amino acids 374-513 of SEQ ID NO:4, amino acids 382-513 of SEQ ID NO:4, amino acids 388-513 of SEQ ID NO:4, or amino acids 412-513 of SEQ ID NO:4. The polypeptide can be a recombinant polypeptide.

In one embodiment, the methods include administering a BMP-7 polypeptide in an amount sufficient to promote BAT differentiation and/or reduce WAT adipogenesis in the subject. The BMP-7 polypeptide is preferably human, and preferably a mature BMP-7 polypeptide, e.g., a BMP-7 polypeptide that includes amino acids 293-431 of SEQ ID NO:5. The polypeptide can be a recombinant polypeptide.

The polypeptide can be administered, e.g., orally, intravenously, percutaneously, subcutaneously, or implanted at a chosen site, e.g., in an adipose tissue of the subject. The polypeptide may be modified, e.g., to increase circulatory half-life, increase cellular uptake, improve distribution to target tissues (e.g., adipose tissue), decrease clearance and/or decrease immunogenicity, e.g., as described herein. In some embodiments, the BMP-2, -4, -5, -6, and/or -7 is administered in combination with another agent, e.g., another BMP protein (e.g., BMP-1 or BMP-3), PPARγ, Retinoid X receptor, alpha (RxRa), insulin, T3, a TZD, vitamin A, retinoic acid, insulin, glucocorticoid or agonist thereof, Wnt, IGF, or other growth factor, e.g., EGF, FGF, TGFα, TGFβ, TNFα, MCSF, VEGF and/or PDFG. In some embodiments, the agent can be a BMP-2, -4, -5, -6, and/or -7 protein as described herein, or an active portion thereof linked with a heterologous polypeptide sequence, e.g., a second BMP protein, to form a chimeric molecule or fusion protein.

In one embodiment, the method can include contacting a cell, e.g., a cultured preadipocyte or adipocyte with the agent in an amount sufficient to increase BAT differentiation or inhibit WAT, and thereafter implanting the cell or cell population in a subject. In another embodiment, the agent is a cell, e.g., a cultured preadipocyte, adipocyte, fibroblast, or epithelial cell, that is genetically engineered in vitro to express a BMP-2, -4, -5, -6, and/or -7 polypeptide, and then administered to the subject. The cells can be autologous, allogeneic or xenogeneic, but are preferably autologous. The cells can be implanted directly or can be administered in a scaffold, matrix, or other implantable device to which the cells can attach (examples include carriers made of, e.g., collagen, fibronectin, elastin, cellulose acetate, cellulose nitrate, polysaccharide, fibrin, gelatin, and combinations thereof).

In some embodiments, the agent is a nucleic acid encoding a BMP-2, -4, -5, -6, and/or -7 polypeptide, or a biologically active fragment or analog thereof.

In one embodiment, the methods include administering the agent in combination with a second treatment, e.g., a second treatment for obesity or a related disorder such as diabetes. For example, the second treatment can be insulin, Orlistat, Phendimetrazine, and/or Phentermine. In some embodiments, the methods include administering one or more other compounds in addition to the BMP, e.g., PPAR(, Retinoid X receptor, alpha (RxRa), insulin, T3, a TZD, retinoic acid, or other compound.

In some embodiments, the methods include evaluating the subject for one or more of: weight, adipose tissue stores, adipose tissue morphology, insulin levels, insulin metabolism, glucose levels, thermogenic capacity, and cold sensitivity. The evaluation can be performed before, during, and/or after the administration of the agent. For example, the evaluation can be performed at least 1 day, 2 days, 4, 7, 14, 21, 30 or more days before and/or after the administration.

In some embodiments, the administration of an agent that increases BMP-2, -4, -5, -6, and/or -7 expression, levels or activity can be initiated: when the subject begins to show signs of a weight related disorder; when a weight related disorder (e.g., obesity) is diagnosed; at the time a treatment for a weight related disorder is begun or begins to exert its effects; or generally, as is needed to maintain health.

The period over which the agent is administered (or the period over which clinically effective levels are maintained in the subject) can be long term, e.g., for six months or more or a year or more, or short term, e.g., for less than a year, six months, one month, two weeks or less.

An agent that increases BMP-2, -4, -5, -6, and/or -7 signaling, to thereby reduce WAT adipogenesis and/or increase BAT differentiation can be, e.g., (a) a BMP-2, -4, -5, -6, and/or -7 polypeptide or a functional fragment or variant thereof, preferably an active (e.g., BMPR-I and/or BMPR-II activating) BMP-2, -4, -5, -6, and/or -7 polypeptide or a functional fragment or analog thereof (e.g., a mature BMP-2, -4, -5, -6, and/or -7 polypeptide, e.g., a mature BMP-2, -4, -5, -6, and/or -7 polypeptide described herein); (b) a peptide or protein agonist of BMP-2, -4, -5, -6, and/or -7 that increases the activity, e.g., the BMPR-I and/or BMPR-II activating activity of BMP-2, -4, -5, -6, and/or -7 (e.g., by increasing or stabilizing binding of BMP-2, -4, -5, -6, and/or -7 to its receptor); (c) a small molecule or protein mimetic that mimics BMP-2, -4, -5, -6, and/or -7 signaling activity, e.g., BMPR-I and/or BMPR-II binding activity, or SMAD phosphorylating activity; (d) a small molecule that increases expression of BMP-2, -4, -5, -6, and/or -7, e.g., by binding to the promoter region of the BMP-2, -4, -5, -6, and/or -7 gene; (e) an antibody, e.g., an antibody that binds to and stabilizes or assists the binding of BMP-2, -4, -5, -6, and/or -7 to a BMP-2, -4, -5, -6, and/or -7 binding partner (e.g., a BMP-2, -4, -5, -6, and/or -7 receptor described herein); or (f) a nucleotide sequence encoding a BMP-2, -4, -5, -6, and/or -7 polypeptide or functional fragment or analog thereof. The nucleotide sequence can be a genomic sequence or a cDNA sequence. The nucleotide sequence can include: a BMP-2, -4, -5, -6, and/or -7 coding region; a promoter sequence, e.g., a promoter sequence from a BMP-2, -4, -5, -6, and/or -7 gene or from another gene; an enhancer sequence; untranslated regulatory sequences, e.g., a 5' untranslated region (UTR), e.g., a 5'UTR from a BMP-2, -4, -5, -6, and/or -7 gene or from another gene, a 3' UTR, e.g., a 3'UTR from a BMP-2, -4, -5, -6, and/or -7 gene or from another gene; a polyadenylation site; an insulator sequence. In another embodiment, the level of BMP-2, -4, -5, -6, and/or -7 protein is increased by increasing the level of expression of an endogenous BMP-2, -4, -5, -6, and/or -7 gene, e.g., by increasing transcription of the BMP-2, -4, -5, -6, and/or -7 gene or increasing BMP-2, -4, -5, -6, and/or -7 mRNA stability. In some embodiments, transcription of the BMP-2, -4, -5, -6, and/or -7 gene is increased by: altering the regulatory sequence of the endogenous BMP-2, -4, -5, -6, and/or -7 gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the BMP-2, -4, -5, -6, and/or -7 gene to be transcribed more efficiently.

An agent that decreases BMP-2, -4, -5, -6, and/or -7 signaling to thereby increase WAT adipogenesis or decrease BAT differentiation can be, for example: a BMP-2, -4, -5, -6, and/or -7 binding protein, e.g., a soluble binding protein that binds BMP-2, -4, -5, -6, and/or -7 and inhibits a BMP-2, -4, -5, -6, and/or -7 activity, or inhibits the ability of a BMP-2, -4, -5, -6, and/or -7 to interact with a binding partner; an antibody that specifically binds to the BMP-2, -4, -5, -6, and/or -7 protein, e.g., an antibody that disrupts a the ability of BMP-2, -4, -5, -6, and/or -7 to bind to a binding partner; a mutated inactive BMP-2, -4, -5, -6, and/or -7 or fragment thereof which disrupts a BMP-2, -4, -5, -6, and/or -7 activity (e.g., a dominant negative BMP-2, -4, -5, -6, and/or -7 mutant); a BMP-2, -4, -5, -6, and/or -7 nucleic acid molecule that can bind to a cellular BMP-2, -4, -5, -6, and/or -7 nucleic acid sequence, e.g., mRNA, and inhibit expression of the protein, e.g., an antisense, siRNA molecule or BMP-2, -4, -5, -6, and/or -7 ribozyme; an agent which decreases BMP-2, -4, -5, -6, and/or -7 gene expression, e.g., a small molecule which binds and inhibits the promoter of BMP-2, -4, -5, -6, and/or -7. In another embodiment, BMP-2, -4, -5, -6, and/or -7 is inhibited by decreasing the level of expression of an endogenous BMP-2, -4, -5, -6, and/or -7 gene, e.g., by decreasing transcription of the BMP-2, -4, -5, -6, and/or -7 gene. In some embodiments, transcription of the BMP-2, -4, -5, -6, and/or -7 gene can be decreased by: altering the regulatory sequences of the endogenous BMP-2, -4, -5, -6, and/or -7 gene, e.g., by the addition of a negative regulatory sequence (such as a DNA-biding site for a transcriptional repressor), or by the removal of a positive regulatory sequence (such as an enhancer or a DNA-binding site for a transcriptional activator). In another embodiment, the antibody which binds the BMP-2, -4, -5, -6, and/or -7 is a monoclonal antibody, e.g., a humanized chimeric or human monoclonal antibody. In some embodiments, the BMP-2, -4, -5, -6, and/or -7 is administered in combination with another agent, e.g., another BMP protein (e.g., BMP-1 or BMP-3), PPARγ, Retinoid X receptor, alpha (RxRa), insulin, T3, a TZD, vitamin A, retinoic acid, insulin, glucocorticoid or agonist thereof, Wnt, IGF, or other growth factor, e.g., EGF, FGF, TGFα, TGFβ, TNFα, MCSF, VEGF and/or PDFG.

In another aspect, the invention features a method of making a cell culture enriched in BAT cells, e.g., compared to a reference value. The methods include: providing a plurality of cells, e.g., a plurality of preadipocyte and/or adipocyte cells (e.g., a population of cells in which at least 30%, 40%, preferably 50%, more preferably 60%, 70%, 80%, 90% or more of the cells are preadipocyte and/or adipocyte cells); and contacting the plurality of cells with an agent that increases BMP-2, -4, -5, -6, and/or -7 signaling, e.g., a BMP-2, -4, -5, -6, and/or -7 polypeptide or other agent described herein, in an amount sufficient to promote BAT differentiation. In one embodiment, the methods include administering a BMP-2, -4, -5, -6, and/or -7 polypeptide in an amount sufficient to promote BAT differentiation in the subject. The BMP-2, -4, -5, -6, and/or -7 polypeptide is preferably human, and preferably a mature BMP-2, -4, -5, -6, and/or -7 polypeptide, e.g., a BMP-2, -4, -5, -6, and/or -7 polypeptide as described herein. In some embodiments, the methods include contacting, administering or expressing one or more other compounds in addition to the BMP, e.g., PPARγ, Retinoid X receptor, alpha (RxRa), insulin, T3, a TZD, retinoic acid, or other compound. The method can include evaluating the adipose tissue cells of the culture, e.g., evaluating the cells' morphology, gene expression (e.g., SREBP1, PPARγ1, PGC-1, C/EBPα, C/EBPβγ, LPL/SCD, and/or adipsin expression), thermogenic activity, and/or relative levels of BAT and/or WAT.

In another aspect, the invention features a cell culture. The cell culture includes (a) a cell selected from the group consisting of: a preadipocyte and adipocyte cell, and (b) an agent that increases BMP-2, -4, -5, -6, and/or -7 signaling in the cell, e.g., an exogenous BMP-2, -4, -5, -6, and/or -7 polypeptide, e.g., a BMP-2, -4, -5, -6, and/or -7 polypeptide or other agent described herein. The cell culture can be a population of cells in which at least 30%, 40%, preferably 50%, more preferably 60%, 70%, 80%, 90% or more of the cells are preadipocyte and/or adipocyte cells. In one embodiment, the methods include administering a BMP-2, -4, -5, -6, and/or -7 polypeptide in an amount sufficient to promote BAT differentiation in the culture. The BMP-2, -4, -5, -6, and/or -7 polypeptide is preferably human, and preferably a mature BMP-2, -4, -5, -6, and/or -7 polypeptide, e.g., a BMP-2, -4, -5, -6, and/or -7 polypeptide as described herein.

In another aspect, the invention features a cultured preadipocyte or adipocyte genetically engineered to express a BMP-2, -4, -5, -6, and/or -7 polypeptide, e.g., a BMP-2, -4, -5, -6, and/or -7 polypeptide described herein. The cell is preferably a cultured mammalian cell, e.g., a human cell, e.g., a primary or secondary human cell. In some embodiments, the cell is genetically engineered to express a non-BMP-2, -4, -5, -6, and/or -7 polypeptide, e.g., a second (or more) BMP protein. The expressed BMP-2, -4, -5, -6, and/or -7 polypeptide is preferably human, and preferably a mature BMP-2, -4, -5, -6, and/or -7 polypeptide, e.g., as described herein.

In another aspect, the invention features a cultured preadipocyte or adipocyte comprising an exogenous nucleic acid that inhibits BMP-2, -4, -5, -6, and/or -7 expression, e.g., a BMP-2, -4, -5, -6, and/or -7 antisense or RNAi nucleic acid. The cell is preferably a cultured mammalian cell, e.g., a human cell, e.g., a primary or secondary human cell.

In another aspect, the invention features a method of identifying an agent that modulates adipose tissue development and differentiation, e.g., an agent that promotes BAT differentiation and/or reduces WAT adipogenesis. The methods include: identifying an agent that modulates, e.g., increases, BMP-2, -4, -5, -6, and/or -7 expression levels or activity (e.g., permanently or temporarily); and correlating the ability of an agent to increase BMP-2, -4, -5, -6, and/or -7 expression, levels or activity with the ability to promote BAT differentiation. In one embodiment, the ability of the agent to interact with, e.g., to bind, BMP-2, -4, -5, -6, and/or -7 is evaluated. In another embodiment, the effect of the agent to interact with a BMP-2, -4, -5, -6, and/or -7 regulatory region, e.g., a BMP-promoter, is evaluated.

The method can include correlating the effect of the agent on BMP-2, -4, -5, -6, and/or -7 with a predicted effect of the agent on a mammal, e.g., a human, e.g., by providing (e.g., to the government, a health care provider, insurance company or patient) informational, marketing or instructional material, e.g., print material or computer readable material (e.g., a label or email), related to the agent or its use, identifying the agent as a possible or predicted treatment in a mammal, e.g., a human. The method can include identifying the agent as a treatment or lead compound for a weight related disorder, e.g., in humans, if it increases BMP-2, -4, -5, -6, and/or -7 expression. The identification can be in the form of informational, marketing or instructional material, e.g., as described herein. In one embodiment, the methods include correlating a value for increased BMP-2, -4, -5, -6, and/or -7 expression with ability to treat a weight related disorder described herein, e.g., generating a dataset of the correlation.

In some embodiments, the methods include evaluating, e.g., quantitatively or qualitatively measuring, the effect of the agent on adipose tissue function or development, e.g., evaluating one or more of: BAT and/or WAT differentiation, BAT thermogenic activity, adipose tissue morphology, ratio of BAT to WAT, or weight (of a subject). Evaluating the effect of the agent on adipose function or development can include administering the agent to an experimental mammal, to the adipose tissue of the animal, e.g., an animal model for a weight related disorder described herein. In some embodiments, the evaluation includes entering a value for the evaluation, e.g., into a database or other record.

In some embodiments, the subject is an experimental animal. The animal can be wild-type or a transgenic experimental animal, e.g., a BMP-2, -4, -5, -6, and/or -7 transgenic or knockout rodent, e.g., BMP-2, -4, -5, -6, and/or -7-null mouse. The subject may also be a human. In some embodiments, the evaluating step comprises administering the agent to the subject and evaluating a parameter of adipose function.

In some embodiments, the identifying step includes: (a) providing an agent to a cell, tissue or non-human animal whose genome includes an exogenous nucleic acid that includes a regulatory region of BMP-2, -4, -5, -6, and/or -7, e.g., a BMP-2, -4, -5, -6, and/or -7 promoter, operably linked to a nucleotide sequence encoding a reporter polypeptide (e.g., a light based, e.g., a colorimeteric (e.g., LacZ) or flourescently detectable label, e.g., a fluorescent reporter polypeptide, e.g. GFP, EGFP, BFP, RFP); (b) evaluating the ability of a test agent to modulate the expression of the reporter polypeptide in the cell, tissue or non-human animal; and (c) selecting a test agent that modulates the expression of the reporter polypeptide as an agent that modulates BMP-2, -4, -5, -6, and/or -7. In one embodiment, the cell or tissue is an adipose cell or tissue, e.g., a preadipocyte or adipocyte cell. In another embodiment, the non-human animal is a transgenic animal, e.g., a transgenic rodent, e.g., a mouse, rat or guinea pig, harboring the nucleic acid. In yet another embodiment, a cell, e.g., adipose cell, or adipose tissue is derived from a transgenic animal.

The test agent can be, e.g., a nucleic acid (e.g., an antisense, ribozyme), a polypeptide (e.g., an antibody or antigen-binding fragment thereof), a peptide fragment, a peptidomimetic, or a small molecule (e.g., a small organic molecule with a molecular weight of less than 2000 daltons). In another embodiment, the test agent is a member of a combinatorial library, e.g., a peptide or organic combinatorial library, or a natural product library. In some embodiments, a plurality of test agents, e.g., library members, is tested. Preferably, the test agents of the plurality, e.g., library, share structural or functional characteristics. The test agent can also be a crude or semi-purified extract, e.g., a botanical extract such as a plant extract, or algal extract.

In one embodiment, the methods include two evaluating steps, e.g., the methods include a first step of evaluating the test agent in a first system, e.g., a cell or tissue system, and a second step of evaluating the test agent in a second system, e.g., a second cell or tissue system or in a non-human animal. In other embodiments, the methods include two evaluating steps in the same type of system, e.g., the agent is re-evaluated in a non-human animal after a first evaluation in the same or a different non-human animal. The two evaluations can be separated by any length of time, e.g., days, weeks, months or years.

In another aspect, the invention features methods of evaluating a subject, e.g., determining if a subject is at risk for a weight-related disorder, e.g., weight gain or obesity. The methods include: evaluating the gene structure, expression, protein level or activity of BMP-2, -4, -5, -6, and/or -7 in the subject. The methods include (a) evaluating the level, activity, expression and/or genotype of a BMP-2, -4, -5, -6, and/or -7 molecule in a subject, e.g., in a biological sample of the subject, such as an adipose cell or tissue sample, and (b) correlating an alteration in a BMP-2, -4, -5, -6, and/or -7 molecule, e.g., a less than wild-type level, activity, expression, and/or a mutation of BMP-2, -4, -5, -6, and/or -7 with a risk for or presence of the weight-related disorder, e.g., a weight-related disorder described herein. Correlating means identifying the alteration as a risk or diagnostic factor of the weight-related disorder, e.g., providing a print material or computer readable medium, e.g., an informational, diagnostic, marketing or instructional print material or computer readable medium, e.g., to the subject or to a health care provider, identifying the alteration as a risk or diagnostic factor for the weight-related disorder.

In some embodiments, the methods include diagnosing a subject as being at risk for or having the weight-related disorder. In another embodiment, the methods include prescribing or beginning a treatment for the weight-related disorder in the subject. In some embodiments, the methods include performing a second diagnostic test, e.g., evaluating one or more of: insulin metabolism, glucose metabolism, cold sensitivity, leptin levels.

The subject is preferably a human, e.g., a human with a family history of obesity or diabetes. The biological sample can be a cell sample, tissue sample, or at least partially isolated molecules, e.g., nucleic acids, e.g., genomic DNA, cDNA, mRNA, and/or proteins derived from the subject. Such methods are useful, e.g., for diagnosis of weight-related disorder, e.g., weight-related disorders described herein.

In some embodiments, the methods include one or more of the following:

1) detecting, in a biological sample of the subject, the presence or absence of a mutation that affects the expression of BMP-2, -4, -5, -6, and/or -7, or detecting the presence or absence of a mutation in a region which controls the expression of the gene, e.g., a mutation in the 5' control region, the presence of a mutation being indicative of risk;

2) detecting, in a biological sample of the subject, the presence or absence of a mutation that alters the structure of BMP-2, -4, -5, -6, and/or -7, the presence of a mutation being indicative of risk;

3) detecting, in a biological sample of the subject, the misexpression of BMP-2, -4, -5, -6, and/or -7, at the mRNA level, e.g., detecting a non-wild-type level of a BMP-2, -4, -5, -6, and/or -7 mRNA, non-wild-type levels of BMP-2, -4, -5, -6, and/or -7 mRNA being associated with risk. Detecting misexpression can include ascertaining the existence of at least one of: an alteration in the level of a mRNA transcript of BMP-2, -4, -5, -6, and/or -7 compared to a reference, e.g., as compared to a baseline value or to levels in a subject not at risk for a adipose disorder; the presence of a non-wild-type splicing pattern of a mRNA transcript of the gene; or a non-wild-type level of BMP-2, -4, -5, -6, and/or -7 protein e.g., as compared to a reference, e.g., compared to a baseline value, or to levels in a subject not at risk for a weight-related disorder;

4) detecting, in a biological sample of the subject, the misexpression of BMP-2, -4, -5, -6, and/or -7, at the protein level, e.g., detecting a non-wildtype level of a BMP-2, -4, -5, -6, and/or -7 polypeptide, decreased or increased levels of BMP-2, -4, -5, -6, and/or -7 protein (e.g., compared to a control) being indicative of a risk. For example, the method can include contacting a sample from the subject with an antibody to BMP-2, -4, -5, -6, and/or -7 protein;

5) detecting, in a biological sample of the subject, a polymorphism, e.g., a SNP, in BMP-2, -4, -5, -6, and/or -7, which is associated with a weight-related disorder described herein. In some embodiments the methods include: ascertaining the existence of at least one of: an insertion or a deletion of one or more nucleotides from BMP-2, -4, -5, -6, and/or -7; a point mutation, e.g., a substitution of one or more nucleotides of the gene; a gross chromosomal rearrangement of the gene, e.g., a translocation, inversion, duplication or deletion. In some embodiments, a SNP or haplotype associated with a weight-related disorder described herein risk is detected.

In one embodiment, detecting a mutation or polymorphism can include: (i) providing a probe or primer, e.g., a labeled probe or primer, that includes a region of nucleotide sequence which hybridizes to a sense or antisense sequence from BMP-2, -4, -5, -6, and/or -7, or naturally occurring mutants thereof, or to the 5' or 3' flanking sequences naturally associated with BMP-2, -4, -5, -6, and/or -7; (ii) exposing the probe/primer to nucleic acid of the subject; and (iii) detecting, e.g., by hybridization, e.g., in situ hybridization to the nucleic acid; or amplification of the nucleic acid, the presence or absence of the mutation or polymorphism.

In some embodiments, the methods include contacting a biological sample, e.g., an adipose cell or tissue sample, with a compound or an agent capable of detecting BMP-2, -4, -5, -6, and/or -7 protein or a BMP-2, -4, -5, -6, and/or -7 nucleic acid, such that the presence of BMP-2, -4, -5, -6, and/or -7 nucleic acid or protein is detected in the biological sample.

In some embodiments, the compound or agent is a nucleic acid probe capable of hybridizing to BMP-2, -4, -5, -6, and/or -7 mRNA or an antibody capable of binding to BMP-2, -4, -5, -6, and/or -7 protein.

In some embodiments, the evaluation is used to choose a course of treatment.

In another aspect, the invention features a computer readable record encoded with (a) a subject identifier, e.g., a patient identifier, (b) one or more results from an evaluation of the subject, e.g., a diagnostic evaluation described herein, e.g., the level of expression, level or activity of BMP-2, -4, -5, -6, and/or -7 in the subject, and optionally (c) a value for or related to a disease state, e.g., a value correlated with disease status or risk with regard to loss of adipose function, e.g., BAT deficiency or weight gain. In one embodiment, the invention features a computer medium having a plurality of digitally encoded data records. Each data record includes a value representing the level of expression, level or activity of BMP-2, -4, -5, -6, and/or -7 in a sample, and a descriptor of the sample. The descriptor of the sample can be an identifier of the sample, a subject from which the sample was derived (e.g., a patient), a diagnosis, or a treatment (e.g., a preferred treatment). In some embodiments, the data record further includes values representing the level of expression, level or activity of genes other than BMP-2, -4, -5, -6, and/or -7 (e.g., other genes associated with loss of adipose function, e.g., weight gain, or other genes on an array). The data record can be structured as a table, e.g., a table that is part of a database such as a relational database (e.g., a SQL database of the Oracle or Sybase database environments). The invention also includes a method of communicating information about a subject, e.g., by transmitting information, e.g., transmitting a computer readable record described herein, e.g., over a computer network.

In another aspect, the invention features a method of providing information, e.g., for making a decision with regard to the treatment of a subject having, or at risk for, a disorder described herein. The methods include (a) evaluating the expression, level or activity of BMP-2, -4, -5, -6, and/or -7; optionally (b) providing a value for the expression, level or activity of BMP-2, -4, -5, -6, and/or -7; optionally (c) comparing the provided value with a reference value, e.g., a control or non-disease state reference or a disease state reference; and optionally (d) based, e.g., on the relationship of the provided value to the reference value, supplying information, e.g., information for making a decision on or related to the treatment of the subject.

In some embodiments, the provided value relates to an activity described herein, e.g., to BMP-2, -4, -5, -6, and/or -7 activity described herein.

In some embodiments, the decision is whether to administer a preselected treatment.

In some embodiments, the decision is whether a party, e.g., an insurance company, HMO, or other entity, will pay for all or part of a preselected treatment.

Also featured is a method of evaluating a sample. The methods include providing a sample, e.g., from the subject, and determining a gene expression profile of the sample, wherein the profile includes a value representing the level of expression of BMP-2, -4, -5, -6, and/or -7. The method can further include comparing the value or the profile (i.e., multiple values) to a reference value or reference profile. The gene expression profile of the sample can be obtained by methods known in the art (e.g., by providing a nucleic acid from the sample and contacting the nucleic acid to an array). The method can be used to diagnose loss of adipose function, e.g., decreased or suboptimal BAT function, e.g., obesity, in a subject wherein misexpression of BMP-2, -4, -5, -6, and/or -7, e.g., an decrease in expression of BMP-2, -4, -5, -6, and/or -7, is an indication that the subject has or is disposed to having loss of adipose function, e.g., obesity. The method can be used to monitor a treatment for loss of adipose function, in a subject. For example, the gene expression profile can be determined for a sample from a subject undergoing treatment. The profile can be compared to a reference profile or to a profile obtained from the subject prior to treatment or prior to onset of the disorder (see, e.g., Golub et al., Science 286:531 (1999)).

DETAILED DESCRIPTION

Figure 1:
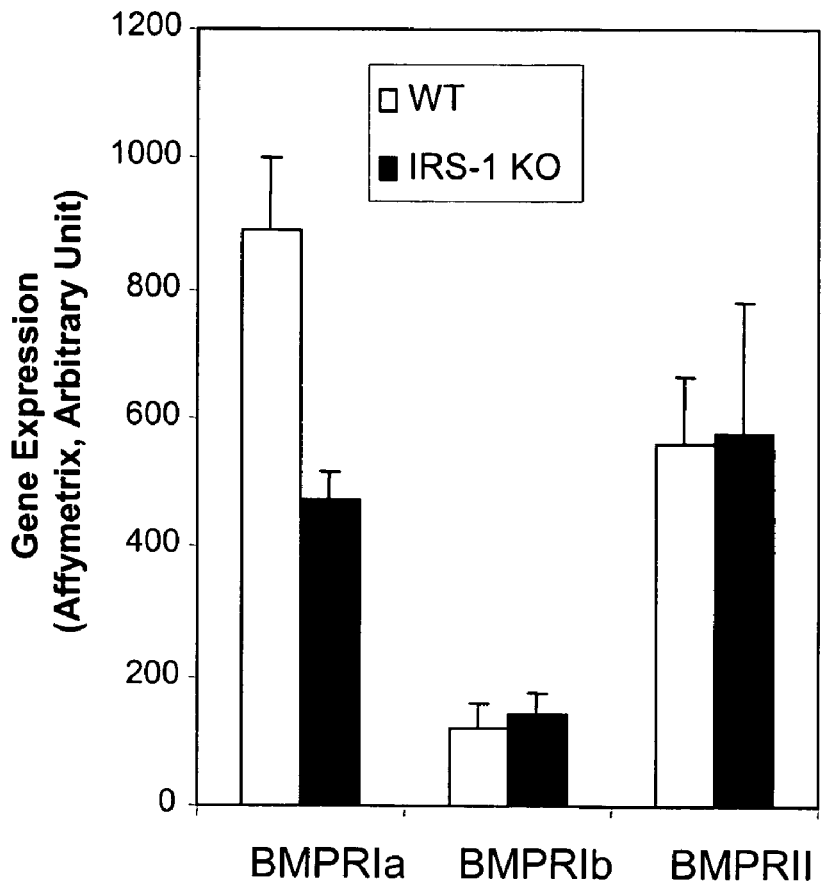
FIG. 1 is a bar graph showing levels of BMP Receptors Ia, Ib, and II in wild type and IRS-1 knockout brown preadipocytes.

As described herein, BMP-2, -4, -5, -6, and -7 are involved in adipocyte differentiation. Specifically, BMP-2, -4, -5, -6, and -7 promote brown adipocyte (BAT) differentiation and inhibit white (WAT) adipogenesis. BMP-2, -4, -5, -6, and/or -7 are thus therapeutic, diagnostic and drug discovery targets for adipose-related disorders, such as obesity and related disorders such as diabetes, insulin resistance, hyperglycemia, hyperlipidemia, and hypercholesterolemia.

Adipose Tissue

The most commonly known fat cells are white fat cells, also known as white adipose tissue (WAT) cells, which have a thin ring of cytoplasm surrounding a lipid or fat droplet. WAT is found underneath the skin and provides heat insulation, cushioning against shock and jarring, and energy reserves. An average lean person has roughly 20 to 40 billion WAT cells. An obese person can have up to ten times more WAT than the average lean person.

The less common fat cells are the brown fat cells, also known as brown adipose tissue (BAT) cells. Energy expenditure for thermogenesis in BAT serves either to maintain body temperature in the cold or to waste food energy. It has roles in thermal balance and energy balance, and when defective, is usually associated with obesity. BAT is typically atrophied in obese animals. The importance of BAT in overall energy homeostasis is underscored by the finding that ablation of BAT in mice results in severe obesity accompanied by insulin resistance, hyperglycemia, hyperlipidemia, and hypercholesterolemia (Lowell at al., Nature 366 (6457):740-2, 1993; Hamann et al., Diabetes. 44 (11):1266-73, 1995; Hamann et al., Endocrinology 137 (1):21-9, 1996.

Adipose tissues contain a potential mitotic compartment, which can allow for growth and differentiation of WAT or BAT cells. Adipose tissue can be readily assayed using routine techniques. An exemplary assay for adipose cells is the Oil Red O lipophilic red dye assay. The dye is used to stain neutral lipids in cells. The amount of staining is directly proportional to the amount of lipid in the cell and can be measured spectrophotometrically. The amount of lipid accumulation is determined as a parameter of differentiation. WAT and BAT can be distinguished by routine techniques, e.g., morphologic changes specific to WAT or BAT, or evaluation of WAT-specific or BAT-specific markers. For example, BAT cells can be identified by expression of uncoupling protein (UCP), e.g., UCP-1.

BMPs

BMP proteins have been used in the clinic in the treatment of bone and cartilage disorders or wounds. The effective clinical use of recombinant BMPs is discussed in Einhorn, J. Bone and Joint Surgery 85A:82-88 (2003), and Sandhu, Spine 28 (15):S64-73 (2003). A BMP polypeptide (e.g., a mature BMP polypeptide) is itself is a viable therapeutic agent because BMPs are small secreted proteins that are internalized into their target cells where they exert their activity.

BMP-2

BMP-2 is 396 amino acids in length, localized to chromosome 20p12 in human. The nucleotide and amino acid sequences of human BMP-2 are disclosed in Wozney et al., Science 242 (4885):1528-1534 (1988). BMP2 belongs to the transforming growth factor-beta (TGFB) superfamily. Bone morphogenetic protein induces bone formation, and BMP2 is a candidate gene for the autosomal dominant disease of fibrodysplasia (myositis) ossificans progressive. Bone morphogenetic protein 2 regulates myogenesis through dosage-dependent PAX3 expression in pre-myogenic cells, and is expressed in mesoderm under SHM control through the SOX9.

The human BMP-2 is shown below. Amino acids 38-268 are the TGF-beta propeptide domain, and 291-396 are the TGF-beta family N-terminal domain. Amino acids 283-396 are the mature peptide. The sequence is set forth in Wozney et al., Science 242:1528-1534 (1988).

(SEQ ID NO:1)

```
  1 MVAGTRCLLA LLLPQVLLGG AAGLVPELGR RKFAAASSGR PSSQPSDEVL SEFELRLLSM

61 FGLKQRPTPS RDAVVPPYML DLYRRHSGQP GSPAPDHRLE RAASRANTVR SFHHEESLEE

121 LPETSGKTTR RFFFNLSSIP TEEFITSAEL QVFREQMQDA LGNNSSFHHR INIYEIIKPA

181 TANSKFPVTR LLDTRLVNQN ASRWESFDVT PAVMRWTAQG HANHGFVVEV AHLEEKQGVS

241 KRHVRISRSL HQDEHSWSQI RPLLVTFGHD GKGHPLHKRE KRQAKHKQRK RLKSSCKRHP

301 LYVDFSDVGW NDWIVAPPGY HAFYCHGECP FPLADHLNST NHAIVQTLVN SVNSKIPKAC

361 CVPTELSAIS MLYLDENEKV VLKNYQDMVV EGCGCR
```

The mature form of BMP-2 contains four potential N-linked glycosylation sites per polypeptide chain, and four potential disulfide bridges. See UniProt entry No. P12643.

BMP-4

BMP-4 induces cartilage and bone formation, and is important in mesoderm induction, tooth development, limb formation and fracture repair. The sequence of the BMP-4 preproprotein is shown below. Amino acids 41-276 are the TGF-beta propeptide domain, and 302-408 are the TGF-beta family N-terminal domain. Amino acids 293-408 are the mature peptide. The sequence is set forth in Wozney et al., Science 242:1528-1534 (1988).

```
                                                            (SEQ ID NO:2)
  1  MIPGNRMLMV  VLLCQVLLGG  ASHASLIPET  GKKKVAEIQG  HAGGRRSGQS  HELLRDFEAT

61  LLQMFGLRRR  PQPSKSAVIP  DYMRDLYRLQ  SGEEEEEQIH  STGLEYPERP  ASRANTVRSF

121  HHEEHLENIP  GTSENSAFRF  LFNLSSIPEN  EAISSAELRL  FREQVDQGPD  WERGFHRINI

182  YEVMKPPAEV  VPGHLITRLL  DTRLVHHNVT  RWETFDVSPA  VLRWTREKQP  NYGLAIEVTH

241  LHQTRTHQGQ  HVRISRSLPQ  GSGNWAQLRP  LLVTFGHDGR  GHALTRRRRA  KRSPKHHSQR

301  ARKKNKNCRR  HSLYVDFSDV  GWNDWIVAPP  GYQAFYCHGD  CPFPLADHLN  STNHAIVQTL

361  VNSVNSSIPK  ACCVPTELSA  ISMLYLDEYD  KVVLKNYQEM  VVEGCGCR
```

The mature form of BMP-4 contains four potential N-linked glycosylation sites per polypeptide chain. A variant exists in which V152 is an A. See UniProt Accession No. P12644.

BMP-5

The BMP-5 preproprotein is a 454 amino acid protein, as shown below. BMP-5 induces cartilage and bone formation. The sequence is set forth in Celeste et al., Proc. Natl. Acad. Sci. U.S.A., 87, 9843-9847, 1990.

```
                                                            (SEQ ID NO:3)
  1  MHLTVFLLKG  IVGFLWSCWV  LVGYAKGGLG  DNHVHSSFIY  RRLRNHERRE  IQREILSILG

61  LPHRPRPFSP  GKQASSAPLF  MLDLYNAMTN  EENPEESEYS  VRASLAEETR  GARKGYPASP

121  NGYPRRIQLS  RTTPLTTQSP  PLASLHDTNF  LNDADMVMSF  VNLVERDKDF  SHQRRHYKEF

181  RFDLTQIPHG  EAVTAAEFRI  YKDRSNNRFE  NETIKISIYQ  IIKEYTNRDA  DLFLLDTRKA

241  QALDVGWLVF  DITVTSNHWV  INPQNNLGLQ  LCAETGDGRS  INVKSAGLVG  RQGPQSKQPF

301  MVAFFKASEV  LLRSVRAANK  RKNQNRNKSS  SHQDSSRMSS  VGDYNTSEQK  QACKKHELYV

361  SFRDLGWQDW  IIAPEGYAAF  YCDGECSFPL  NAHMNATNHA  IVQTLVHLMF  PDHVPKPCCA

421  PTKLNAISVL  YFDDSSNVIL  KKYRNMVVRS  CGCH
```

The mature BMP-5 protein is believed to be amino acids 323-454 of SEQ ID NO:3, and has four potential N-linked glycosylation sites per polypeptide chain, and four potential disulfide bridges. See UniProt Accession Nos. P22003; Q9H547; or Q9NTM5.

BMP-6

BMP-6 is an autocrine stimulator of chondrocyte differentiation, and is involved in the development of embryonic neural, and urinary systems, as well as growth and differentiation of liver and keratinocytes. BMP-6 knockout mice are viable and show a slight delay in ossification of the sternum. BMP-6 (precursor) is a 57 kD protein, 513 amino acids in length, localized to chromosome 6p24 in human. The nucleotide and amino acid sequence of human BMP-6 is disclosed in U.S. Pat. No. 5,187,076. BMP-6 is predicted to be synthesized as a precursor molecule which is cleaved to yield a 132 amino acid mature polypeptide with a calculated molecular weight of approximately 15 Kd. The mature form of BMP-6 contains three potential N-linked glycosylation sites per polypeptide chain. The active BMP-6 protein molecule is likely a dimer. Processing of BMP-6 into the mature form involves dimerization and removal of the N-terminal region in a manner analogous to the processing of the related protein TGFβ (Gentry et al., Molec. Cell. Biol. 8:4162 (1988); Dernyck et al., Nature 316:701 (1985)). The human BMP-6 precursor is shown below. The mature polypeptide is believed to include amino acids 374-513 of SEQ ID NO:4. Other active BMP-6 polypeptides include polypeptides including amino acids 382-513, 388-513 and 412-513 of SEQ ID NO:4.

```
                                                                    (SEQ ID NO:4)
    MPGLGRRAQW LCWWWGLLCS CCGPPPLRPP LPAAAAAAG GQLLGDGGSP GRTEQPPPSP  61

QSSSGFLYRR LKTQEKREMQ KEILSVLGLP HRPRPLHGLQ QPQPPALRQQ EEQQQQQQLP 121

RGEPPPGRLK SAPLFMLDLY NALSADNDED GASEGERQQS WPHEAASSSQ RRQPPPGAAH 181

PLNRKSLLAP GSGSGGASPL TSAQDSAFLN DADMVMSFVN LVEYDKEFSP RQRHHKEFKF 241

NLSQIPEGEV VTAAEFRIYK DCVMGSFKNQ TFLISIYQVL QEHQHRDSDL FLLDTRVVWA 301

SEEGWLEFDI TATSNLWVVT PQHNMGLQLS VVTRDGVHVH PRAAGLVGRD GPYDKQPFMV 361

AFFKVSEVHV RTTRSASSRR RQQSRNRSTQ SQDVARVSSA SDYNSSELKT ACRKHELYVS 421

FQDLGWQDWI IAPKGYAANY CDGECSFPLN AHMNATNHAI VQTLVHLMNP EYVPKPCCAP 481

TKLNAISVLY FDDNSNVILK KYRNMVVRAC GCH
```

The human BMP-6 promoter has been characterized (See Tamada et al., Biochim Biophys Acta. 1998, 1395 (3):247-51), and can be used in methods described herein. See UniProt Accession No. P22004.

Administration, antisense treatment, and quantitation of BMP-6 are described in Boden et al. (Endocrinology Vol. 138, No. 7 2820-2828).

BMP-7

BMP-7 also belongs to the TGF-beta superfamily. It induces cartilage and bone formation, and may be the osteoinductive factor responsible for the phenomenon of epithelial osteogenesis. BMP-7 plays a role in calcium regulation and bone homeostasis, and in the regulation of anti-inflammatory response in the adult gut tissue. The sequence of BMP-7 is shown below:

```
                                                                    (SEQ ID NO:5)
  1 MHVRSLRAAA PHSFVALWAP LFLLRSALAD FSLDNEVHSS FIHRRLRSQE RREMQREILS

61 ILGLPHRPRP HLQGKHNSAP MFMLDLYNAM AVEEGGGPGG QGFSYPYKAV FSTQGPPLAS

121 LQDSHFLTDA DMVMSFVNLV EHDKEFFHPR YHHREFRFDL SKIPEGEAVT AAEFRIYKDY

181 IRERFDNETF RISVYQVLQE HLGRESDLFL LDSRTLWASE EGWLVFDITA TSNHWVVNPR

241 HNLGLQLSVE TLDGQSINPK LAGLIGRHGP QNKQPFMVAF FKATEVHFRS IRSTGSKQRS

301 QNRSKTPKNQ EALRMANVAE NSSSDQRQAC KKHELYVSFR DLGWQDWIIA PEGYAAYYCE

361 GECAFPLNSY MNATNHAIVQ TLVHFINPET VPKPCCAPTQ LNAISVLYFD DSSNVILKKY

421 RNMVVRACGC H
```

Amino acids 1-29 are a potential signal sequence; 30-431 are the prepropeptide, and 293-431 are the mature protein. The mature form of BMP-2 contains four potential N-linked glycosylation sites per polypeptide chain, and four potential disulfide bridges. See UniProt Accession No. P18075.

Pharmacokinetic Properties and Therapeutic Activity

Modifications can be made to a protein that result in pharmacokinetic properties of the protein which are desirable for use in protein therapy. For example, such modifications can result in longer circulatory half-life, an increase in cellular uptake, improved distribution to targeted tissues, a decrease in clearance and/or a decrease of immunogenicity. Several art-recognized approaches useful to optimize the therapeutic activity of a protein, e.g., a therapeutic protein described herein, e.g., a BMP-2, -4, -5, -6, and/or -7 polypeptide, are summarized below.

Expression System

For recombinant proteins, the choice of expression system can influence pharmacokinetic characteristics. Differences between expression systems in post-translational processing lead to recombinant proteins of varying molecular size and charge, which can affect circulatory half-life, rate of clearance and immunogenicity, for example. The pharmacokinetic properties of the protein may be optimized by the appropriate selection of an expression system, such as selection of a bacterial, viral, or mammalian expression system. Exemplary mammalian cell lines useful in expression systems for therapeutic proteins are Chinese hamster ovary, (CHO) cells, the monkey COS-1 cell line and the CV-1 cell line.

Chemical Modification

A protein can be chemically altered to enhance the pharmacokinetic properties while maintaining activity. The protein can be covalently linked to a variety of moieties, altering the molecular size and charge of the protein and consequently its pharmacokinetic characteristics. The moieties are preferably non-toxic and biocompatible. In one embodiment, polyethylene glycol (PEG) can be covalently attached to the protein (PEGylation). PEG is a class of polymers comprised of repeating ethylene oxide subunits with terminal hydroxyl groups. A variety of PEG molecules are known and/or commercially available (See, e.g., Sigma-Aldrich catalog). PEG molecules are available in various lengths, molecular weights, and substitution patterns, and may be linear or branched. PEG is attached to the protein via an activated terminal hydroxyl group; preferably, the hydroxyl group is activated as an ester, carbonate, aldehyde or tresylate. The activated hydroxyl reacts with nucleophilic groups on the protein, forming a linkage between the protein and PEG. Often the nucleophilic group is the amino group of a lysine or the N-terminus of the protein. One or multiple chains of PEG may be attached to the protein. The choice of site(s) and functionality of the linkage of PEGylation and the choice of PEG molecule can be optimized to achieve the desired pharmacokinetic properties. PEGylation can increase the stability of the protein, decrease immunogenicity by steric masking of epitopes, and improve half-life by decreasing glomerular filtration. (See, e.g., *Poly(ethylene glycol): chemistry and biological applications*, Harris and Zalipsky, eds., ACS Symposium Series, No. 680, 1997; Harris et al., Clinical Pharmacokinetics 40:7, 485-563 (2001)). Examples of therapeutic proteins administered as PEG constructs include Adagen (PEG-ADA) and Oncospar (Pegylated asparaginase). In another embodiment, the protein can be similarly linked to oxidized dextrans via an amino group. (See Sheffield, Current Drug Targets—Cardiovas. and Haemat. Dis. 1:1, 1-22 (2001)).

Furthermore, the therapeutic protein can be chemically linked to another protein. The therapeutic protein can be cross-linked carrier protein to form a larger molecular weight complex with longer circulatory half-life and improved cellular uptake. In one embodiment, the carrier protein can be a serum protein, such as albumin. The therapeutic protein can be attached to one or more albumin molecules via a bifunctional cross-linking reagent. The cross-linking reagent may be homo- or heterofunctional. In another embodiment, the therapeutic protein can cross-link with itself to form a homodimer, trimer, or higher analog. Again, either heterobifunctional or homobifunctional cross-linking reagents can be used to form the dimers or trimers. (See Stykowski et al., Proc. Natl. Acad. Sci. USA, 95, 1184-1188 (1998)). Increasing the molecular weight and size of the therapeutic protein through dimerization or trimerization can decrease clearance.

Modification of Protein Formulation

The formulation of the protein may also be changed. The therapeutic protein can be formulated in a carrier system.

The carrier can be a colloidal system. The colloidal system can be liposome, a phospholipid bilayer vehicle. In one embodiment, the therapeutic protein is encapsulated in a liposome while maintaining protein integrity. As one skilled in the art would appreciate, there are a variety of methods to prepare liposomes. (See Lichtenberg et al., Methods Biochem Anal, 33:337-462 (1988), LIPOSOME TECHNOLOGY Anselem et al., CRC Press, 1993). Liposomes can be prepared from an assortment of phospholipids varying in size and substitution, and may also contain additional components with low toxicity, such as cholesterol. The liposome can be formulated and isolated in a variety of shapes and sizes. Additionally, moieties may attached to the surface of the liposome to further enhance the pharmacokinetic properties of the carrier. The moieties may be attached to phospholipid or cholesterol molecules, and the percentage of the moiety incorporated on the surface may be adjusted for optimal liposome stability and pharmacokinetic characteristics. One embodiment comprises a liposome with poly-ethylene glycol (PEG) added to the surface. Liposomal formulations can delay clearance and increase cellular uptake. (See Reddy, Annals of Pharmacotherapy, 34:7/8, 915-923 (2000)).

The carrier can also be a polymer, e.g., a biodegradable, biocompatible polymer matrix. In one embodiment, the therapeutic protein can be embedded in the polymer matrix while maintaining protein integrity. The polymer may be natural, such as polypeptides, proteins or polysaccharides, or synthetic, such as poly($\alpha$-hydroxy) acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, Annals of Pharmacotherapy, 34:7/8, 915-923 (2000)). A polymer formulation for human growth hormone (hGH) has been used in clinical trials. (See Kozarich and Rich, Chemical Biology 2:548-552 (1998)). Examples of polymer microsphere sustained release formulations are described in PCT publication WO 99/15154 (Tracy et al.), U.S. Pat. Nos. 5,674,534 and 5,716,644 (both to Zale et al.), PCT publication WO 96/40073 (Zale et al.), and PCT publication WO 00/38651 (Shah et al.). U.S. Pat. Nos. 5,674,534 and 5,716,644 and PCT publication WO 96/40073 describe a polymeric matrix containing particles of erythropoietin that are stabilized against aggregation with a salt.

Administration

An agent that modulates BMP-2, -4, -5, -6, and/or -7 signaling, e.g., an agent described herein, such as a BMP-2, -4, -5, -6, and/or -7 polypeptide, can be administered to a subject by standard methods. For example, the agent can be administered by any of a number of different routes including intravenous, intradermal, subcutaneous, percutaneous injection, oral (e.g., inhalation), transdermal (topical), and transmucosal. In one embodiment, the modulating agent can be administered orally. In another embodiment, the agent is administered by injection, e.g., intramuscularly, or intravenously. The agent can be encapsulated or injected, e.g., in a viscous form, for delivery to a chosen site, e.g., a site of adipose tissue, e.g., a subcutaneous or omentum adipose pad. The agent can be provided in a matrix capable of delivering the agent to the chosen site. Matrices can provide slow release of the agent and provide proper presentation and appropriate environment for cellular infiltration. Matrices can be formed of materials presently in use for other implanted medical applications. The choice of matrix material is based on any one or more of: biocompatibility, biodegradability, mechanical properties, cosmetic appearance and interface properties. One example is a collagen matrix.

The agent, e.g., a BMP-2, -4, -5, -6, and/or -7 polypeptide, nucleic acid molecule, analog, mimetic or modulators (e.g., organic compounds or antibodies (also referred to herein as "active compounds") can be incorporated into pharmaceutical compositions suitable for administration to a subject, e.g., a human. Such compositions typically include the polypeptide, nucleic acid molecule, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an agent described herein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL™ (sodium carboxymethyl starch), or corn starch; a lubricant such as magnesium stearate or STEROTES™; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid.

Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The nucleic acid molecules described herein can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al., PNAS 91:3054-3057 (1994)). The pharmaceutical preparation of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

In some embodiments, the pharmaceutical composition is injected into a tissue, e.g., an adipose tissue.

Gene Therapy

The nucleic acids described herein, e.g., an antisense nucleic acid described herein, or BMP-2, -4, -5, -6, and/or -7 polypeptide encoding nucleic acid, can be incorporated into a gene construct to be used as a part of a gene therapy protocol to deliver nucleic acids encoding either an agonistic or antagonistic form of an agent described herein, e.g., BMP-2, -4, -5, -6, and/or -7. The invention features expression vectors for in vivo transfection and expression of a BMP-2, -4, -5, -6, and/or -7 polypeptide described herein in particular cell types. Expression constructs of such components may be administered in any biologically effective carrier, e.g. any formulation or composition capable of effectively delivering the component gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (e.g., LIPOFECTIN™) or derivatized (e.g. antibody conjugated), polylysine conjugates, gramicidin S, artificial viral envelopes or other such intracellular carriers, as well as direct injection of the gene construct or $CaPO_4$ precipitation carried out in vivo.

One approach for in vivo introduction of nucleic acid into a cell is by use of a viral vector containing nucleic acid, e.g. a cDNA, encoding an alternative pathway component described herein. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, Blood 76:271-78 (1990)). A replication defective retrovirus can be packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel et al. (eds.) Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include *Crip, *Cre, *2 and *Am. Retroviruses have been used to introduce a variety of genes into many different cell types, including epithelial cells, in vitro and/or in vivo (see for example Eglitis, et al., Science 230:1395-1398 (1985); Danos and Mulligan, Proc. Natl. Acad. Sci. USA 85:6460-6464 (1988); Wilson et al., Proc. Natl. Acad. Sci. USA 85:3014-3018 (1988); Armentano et al., Proc. Natl. Acad. Sci. USA 87:6141-6145 (1990); Huber et al., Proc. Natl. Acad. Sci. USA 88:8039-8043 (1991); Ferry et al., Proc. Natl. Acad. Sci. USA 88:8377-8381 (1991); Chowdhury et al., Science 254:1802-1805 (1991); van Beusechem et al., Proc. Natl. Acad. Sci. USA 89:7640-7644 (1992); Kay et al., Human Gene Therapy 3:641-647 (1992); Dai et al., Proc. Natl. Acad. Sci. USA 89:10892-10895 (1992); Hwu et al., J. Immunol. 150:4104-4115 (1993); U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting non-dividing cells and can be used to infect a wide variety of cell types, including epithelial cells (Rosenfeld et al. (1992), supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. (1998), supra; Haj-Ahmand and Graham, J. Virol. 57:267 (1986)).

Yet another viral vector system useful for delivery of the subject gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol. 158:97-129 (1992)). It is also one of the few viruses that may integrate its DNA into non-dividing cells, and exhibits a high frequency of stable integration (see for example Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989)). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993)).

In addition to viral transfer methods, such as those illustrated above, non-viral methods can also be employed to cause expression of an nucleic acid agent described herein (e.g., a BMP-2, -4, -5, -6, and/or -7 polypeptide encoding nucleic acid) in the tissue of a subject. Most nonviral methods of gene transfer rely on normal mechanisms used by mammalian cells for the uptake and intracellular transport of macromolecules. In some embodiments, non-viral gene delivery systems of the present invention rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems such as are described in Meuli et al., J. Invest. Dermatol. 116(1):131-135 (2001); Cohen et al., Gene Ther 7 (22):1896-905 (2000); or Tam et al., Gene Ther. 7 (21):1867-74 (2000).

In a representative embodiment, a gene encoding an alternative pathway component described herein can be entrapped in liposomes bearing positive charges on their surface (e.g., lipofectins) and (optionally) which are tagged with antibodies against cell surface antigens of the target tissue (Mizuno et al., No Shinkei Geka 20:547-551 (1992); PCT publication WO91/06309; Japanese patent application 1047381; and European patent publication EP-A-43075).

In clinical settings, the gene delivery systems for the therapeutic gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al., PNAS 91: 3054-3057 (1994)).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

Cell Therapy

An agent described herein for increasing BMP-2, -4, -5, -6, and/or -7 signaling, e.g., a BMP-2, -4, -5, -6, and/or -7 polypeptide or active fragment thereof, can also be increased in a subject by introducing into a cell, e.g., an adipose cell, a nucleotide sequence that encodes a BMP-2, -4, -5, -6, and/or -7 polypeptide. The nucleotide sequence can be a BMP-2, -4, -5, -6, and/or -7 encoding sequence or active fragment thereof, and any of: a promoter sequence, e.g., a promoter sequence from a BMP-2, -4, -5, -6, and/or -7 gene or from another gene; an enhancer sequence, e.g., 5' untranslated region (UTR), e.g., a 5' UTR from a BMP-2, -4, -5, -6, and/or -7 gene or from another gene, a 3' UTR, e.g., a 3' UTR from a BMP-2, -4, -5, -6, and/or -7 gene or from another gene; a polyadenylation site; an insulator sequence; or another sequence that modulates the expression of BMP-2, -4, -5, -6, and/or -7. The cell can then be introduced into the subject.

Primary and secondary cells to be genetically engineered can be obtained from a variety of tissues and include cell types which can be maintained and propagated in culture. For example, primary and secondary cells include adipose cells, fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells (myoblasts) and precursors of these somatic cell types. Primary cells are preferably obtained from the individual to whom the genetically engineered primary or secondary cells are administered. However, primary cells may be obtained for a donor (other than the recipient).

The term "primary cell" includes cells present in a suspension of cells isolated from a vertebrate tissue source (prior to their being plated i.e., attached to a tissue culture substrate such as a dish or flask), cells present in an explant derived from tissue, both of the previous types of cells plated for the first time, and cell suspensions derived from these plated cells. The term "secondary cell" or "cell strain" refers to cells at all subsequent steps in culturing. Secondary cells are cell strains which consist of secondary cells which have been passaged one or more times.

Primary or secondary cells of vertebrate, particularly mammalian, origin can be transfected with an exogenous nucleic acid sequence which includes a nucleic acid sequence encoding a signal peptide, and/or a heterologous nucleic acid sequence, e.g., encoding BMP-2, -4, -5, -6, and/or -7, or an agonist or antagonist thereof, and produce the encoded product stably and reproducibly in vitro and in vivo, over extended periods of time. A heterologous amino acid can also be a regulatory sequence, e.g., a promoter, which causes expression, e.g., inducible expression or upregulation, of an endogenous sequence. An exogenous nucleic acid sequence can be introduced into a primary or secondary cell by homologous recombination as described, for example, in U.S. Pat. No. 5,641,670, the contents of which are incorporated herein by reference. The transfected primary or secondary cells may also include DNA encoding a selectable marker which confers a selectable phenotype upon them, facilitating their identification and isolation.

Vertebrate tissue can be obtained by standard methods such a punch biopsy or other surgical methods of obtaining a tissue source of the primary cell type of interest. For example, punch biopsy is used to obtain skin as a source of fibroblasts or keratinocytes. A mixture of primary cells is obtained from the tissue, using known methods, such as enzymatic digestion or explanting. If enzymatic digestion is used, enzymes such as collagenase, hyaluronidase, dispase, pronase, trypsin, elastase and chymotrypsin can be used.

The resulting primary cell mixture can be transfected directly or it can be cultured first, removed from the culture plate and resuspended before transfection is carried out. Primary cells or secondary cells are combined with exogenous nucleic acid sequence to, e.g., stably integrate into their genomes, and treated in order to accomplish transfection. As used herein, the term "transfection" includes a variety of techniques for introducing an exogenous nucleic acid into a cell including calcium phosphate or calcium chloride precipitation, microinjection, DEAE-dextrin-mediated transfection, lipofection or electroporation, all of which are routine in the art.

Transfected primary or secondary cells undergo sufficient number doubling to produce either a clonal cell strain or a heterogeneous cell strain of sufficient size to provide the therapeutic protein to an individual in effective amounts. The number of required cells in a transfected clonal heterogeneous cell strain is variable and depends on a variety of factors, including but not limited to, the use of the transfected cells, the functional level of the exogenous DNA in the transfected cells, the site of implantation of the transfected cells (for example, the number of cells that can be used is limited by the anatomical site of implantation), and the age, surface area, and clinical condition of the patient.

The transfected cells, e.g., cells produced as described herein, can be introduced into an individual to whom the product is to be delivered. Various routes of administration and various sites (e.g., renal sub capsular, subcutaneous, central nervous system (including intrathecal), intravascular, intrahepatic, intrasplanchnic, intraperitoneal (including intraomental), intramuscularly implantation) can be used. One implanted in individual, the transfected cells produce the product encoded by the heterologous DNA or are affected by the heterologous DNA itself. For example, an individual who suffers from obesity is a candidate for implantation of cells producing an agent described herein, e.g., a BMP-2, -4, -5, -6, and/or -7 polypeptide or a fragment or analog or mimic thereof as described herein.

An immunosuppressive agent e.g., drug, or antibody, can be administered to a subject at a dosage sufficient to achieve the desired therapeutic effect (e.g., inhibition of rejection of the cells). Dosage ranges for immunosuppressive drugs are known in the art. See, e.g., Freed et al., N. Engl. J. Med. 327:1549 (1992); Spencer et al., N. Engl. J. Med. 327:1541 (1992); Widner et al., N. Engl. J. Med. 327:1556 (1992)). Dosage values may vary according to factors such as the disease state, age, sex, and weight of the individual.

Diagnostic Assays

The diagnostic assays described herein involve evaluating the BMP-2, -4, -5, -6, and/or -7 signaling pathway in the subject, e.g., in a adipose tissue. Various art-recognized methods are available for evaluating the activity of the BMP-2, -4, -5, -6, and/or -7 signaling pathway or components thereof. For example, the method can include evaluating either the level of a BMP-2, -4, -5, -6, and/or -7 pathway component (e.g., the level of BMP-2, -4, -5, -6, and/or -7 receptor or SMAD) and/or an activity of the BMP-2, -4, -5, -6, and/or -7 pathway. Techniques for detection of BMP-2, -4, -5, -6, and/or -7 are known in the art and include, inter alia: antibody based assays such as enzyme immunoassays (EIA), radioimmunoassays (RIA), and Western blot analysis. Typically, the level in the subject is compared to the level and/or activity in a control, e.g., the level and/or activity in a tissue from a non-disease subject.

Techniques for evaluating binding activity, e.g., of BMP-2, -4, -5, -6, and/or -7 to a BMP-2, -4, -5, -6, and/or -7 binding partner, such as its receptor, include fluid phase binding assays, affinity chromatography, size exclusion or gel filtration, ELISA, immunoprecipitation (e.g., the ability of an antibody specific to a first factor, e.g., BMP-2, -4, -5, -6, and/or -7, to co-immunoprecipitate a second factor or complex, e.g., its receptor, with which the first factor can associate in nature).

Another method of evaluating the BMP-2, -4, -5, -6, and/or -7 pathway in a subject is to determine the presence or absence of a lesion in or the misexpression of a gene which encodes a component of the BMP-2, -4, -5, -6, and/or -7 pathway e.g., BMP-2, -4, -5, -6, and/or -7. The methods can include one or more of the following:

detecting, in a tissue of the subject, the presence or absence of a mutation which affects the expression of a gene encoding BMP-2, -4, -5, -6, and/or -7, or detecting the presence or absence of a mutation in a region which controls the expression of the gene, e.g., a mutation in the 5' control region;

detecting, in a tissue of the subject, the presence or absence of a mutation which alters the structure of a gene encoding BMP-2, -4, -5, -6, and/or -7;

detecting, in a tissue of the subject, the misexpression of a gene encoding BMP-2, -4, -5, -6, and/or -7, at the mRNA level, e.g., detecting a non-wild type level of a mRNA;

detecting, in a tissue of the subject, the misexpression of the gene, at the protein level, e.g., detecting a non-wild type level of a BMP-2, -4, -5, -6, and/or -7 polypeptide.

In some embodiments the methods include: ascertaining the existence of at least one of: a deletion of one or more nucleotides from a gene encoding BMP-2, -4, -5, -6, and/or -7; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from a BMP-2, -4, -5, -6, and/or -7 gene, or naturally occurring mutants thereof or 5' or 3' flanking sequences naturally associated with the gene; (ii) exposing the probe/primer to nucleic acid of a tissue; and detecting, by hybridization, e.g., in situ hybridization, of the probe/primer to the nucleic acid, the presence or absence of the genetic lesion.

In some embodiments, detecting the misexpression includes ascertaining the existence of at least one of: an alteration in the level of a messenger RNA transcript of a gene encoding BMP-2, -4, -5, -6, and/or -7; the presence of a non-wild type splicing pattern of a messenger RNA transcript of the gene; or a non-wild type level of a gene encoding BMP-2, -4, -5, -6, and/or -7.

In some embodiments, the methods include determining the structure of a gene encoding BMP-2, -4, -5, -6, and/or -7, an abnormal structure being indicative of risk for the disorder.

In some embodiments the methods include contacting a sample from the subject with an antibody to a component of the alternative pathway protein, such as BMP-2, -4, -5, -6, and/or -7, or a nucleic acid which hybridizes specifically with the gene.

Expression Monitoring and Profiling.

The presence, level, or absence of BMP-2, -4, -5, -6, and/or -7 (protein or nucleic acid) in a biological sample can be evaluated by obtaining a biological sample from a test subject and contacting the biological sample with a compound or an agent capable of detecting the protein or nucleic acid (e.g., mRNA, genomic DNA) that encodes BMP-2, -4, -5, -6, and/ or -7 such that the presence of the protein or nucleic acid is detected in the biological sample. The term "biological sample" includes tissues, cells and biological fluids isolated from a subject, as well as tissues, cells and fluids present within a subject, e.g., urine. Suitable biological samples are serum or urine. The level of expression of BMP-2, -4, -5, -6, and/or -7 can be measured in a number of ways, including, but not limited to: measuring the mRNA encoded by the BMP-2, -4, -5, -6, and/or -7 gene; measuring the amount of protein encoded by BMP-2, -4, -5, -6, and/or -7; or measuring the activity of the protein encoded by the gene.

The level of mRNA corresponding to BMP-2, -4, -5, -6, and/or -7 in a cell can be determined both by in situ and by in vitro formats.

Isolated mRNA can be used in hybridization or amplification assays that include, but are not limited to, Southern or Northern analyses, polymerase chain reaction analyses and probe arrays. One suitable diagnostic method for the detection of mRNA levels involves contacting the isolated mRNA with a nucleic acid molecule (probe) that can hybridize to the mRNA encoded by the gene being detected. The nucleic acid probe can be, for example, a full-length nucleic acid, or a portion thereof, such as an oligonucleotide of at least 7, 15, 30, 50, 100, 250 or 500 nucleotides in length and sufficient to specifically hybridize under stringent conditions to mRNA or genomic DNA of BMP-2, -4, -5, -6, and/or -7. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the gene os a component of the alternative pathway.

The level of mRNA in a sample that is encoded by a gene can be evaluated with nucleic acid amplification, e.g., by rtPCR (Mullis U.S. Pat. No. 4,683,202), ligase chain reaction (Barany, Proc. Natl. Acad. Sci. USA 88:189-193 (1991)), self sustained sequence replication (Guatelli et al., Proc. Natl. Acad. Sci. USA 87:1874-1878 (1990)), transcriptional amplification system (Kwoh et al., Proc. Natl. Acad. Sci. USA 86:1173-1177 (1989)), Q-Beta Replicase (Lizardi et al., Bio/Technology 6:1197 (1988)), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the gene being analyzed.

In another embodiment, the methods further contacting a control sample with a compound or agent capable of detecting mRNA, or genomic DNA of a component of the alternative pathway, and comparing the presence of the mRNA or genomic DNA in the control sample with the presence of BMP-2, -4, -5, -6, and/or -7 mRNA or genomic DNA in the test sample. In still another embodiment, serial analysis of gene expression, as described in U.S. Pat. No. 5,695,937, is used to detect transcript levels of BMP-2, -4, -5, -6, and/or -7.

A variety of methods can be used to determine the level of BMP-2, -4, -5, -6, and/or -7 protein. In general, these methods include contacting an agent that selectively binds to the protein, such as an antibody with a sample, to evaluate the level of protein in the sample. In some embodiments, the antibody bears a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect a component of the BMP-2, -4, -5, -6, and/or -7 pathway, e.g., BMP-2, -4, -5, -6, and/or -7, in a biological sample in vitro as well as in vivo. In vitro techniques for detection include enzyme linked immunosorbent assays (ELISAs), immunoprecipitations, immunofluorescence, enzyme immunoassay (EIA), radioimmunoassay (RIA), and Western blot analysis. In vivo techniques for detection of include introducing into a subject a labeled antibody. For example, the antibody can be labeled with a radioactive marker whose presence and location in a subject can be detected by standard imaging techniques. In another embodiment, the sample is labeled, e.g., biotinylated and then contacted to the antibody, e.g., an antibody positioned on an antibody array. The sample can be detected, e.g., with avidin coupled to a fluorescent label.

In another embodiment, the methods further include contacting the control sample with a compound or agent capable of detecting a BMP-2, -4, -5, -6, and/or -7, and comparing the presence of BMP-2, -4, -5, -6, and/or -7 protein in the control sample with the presence of the protein in the test sample.

The invention also includes kits for detecting the presence of BMP-2, -4, -5, -6, and/or -7 in a biological sample. For example, the kit can include a compound or agent capable of detecting BMP-2, -4, -5, -6, and/or -7 protein (e.g., an antibody) or mRNA (e.g., a nucleic acid probe); and a standard. The compound or agent can be packaged in a suitable container. The kit can further comprise instructions for using the kit to evaluate a subject, e.g., for risk or predisposition to diabetes related adipose disease.

The diagnostic methods described herein can identify subjects having, or at risk of developing, adipose-related disorders, such as obesity and diabetes. The prognostic assays described herein can be used to determine whether a subject can be administered an agent (e.g., BMP-2, -4, -5, -6, and/or -7 or another agent described herein) to treat an adipose-related disorder.

Kits

A BMP-2, -4, -5, -6, and/or -7 polypeptide, e.g., a BMP-2, -4, -5, -6, and/or -7 polypeptide described herein, can be provided in a kit. The kit includes (a) BMP-2, -4, -5, -6, and/or -7, e.g., a composition that includes BMP-2, -4, -5, -6, and/or -7, and (b) informational material. The informational material can be descriptive, instructional, marketing or other material that relates to the methods described herein and/or the use of BMP-2, -4, -5, -6, and/or -7 for the methods described herein. For example, the informational material relates to adipose tissue, obesity or diabetes.

In one embodiment, the informational material can include instructions to administer BMP-2, -4, -5, -6, and/or -7 in a suitable manner to perform the methods described herein, e.g., in a suitable dose, dosage form, or mode of administration (e.g., a dose, dosage form, or mode of administration described herein). Suitable doses, dosage forms, or modes of administration are percutaneous, iv, and oral and implantation into an adipose tissue. In another embodiment, the informational material can include instructions to administer BMP-2, -4, -5, -6, and/or -7 to a suitable subject, e.g., a human, e.g., a human having, or at risk for, obesity.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about BMP-2, -4, -5, -6, and/or -7 and/or its use in the methods described herein. Of course, the informational material can also be provided in any combination of formats.

In addition to BMP-2, -4, -5, -6, and/or -7, the composition of the kit can include other ingredients, such as a solvent or buffer, a stabilizer, a preservative, a fragrance or other cosmetic ingredient, and/or a second agent for treating a condition or disorder described herein, e.g., insulin or an obesity drug. Alternatively, the other ingredients can be included in the kit, but in different compositions or containers than BMP-2, -4, -5, -6, and/or -7. In such embodiments, the kit can include instructions for admixing BMP-2, -4, -5, -6, and/or -7 and the other ingredients, or for using BMP-2, -4, -5, -6, and/or -7 together with the other ingredients.

BMP-2, -4, -5, -6, and/or -7 can be provided in any form, e.g., liquid, dried or lyophilized form. It is preferred that BMP-2, -4, -5, -6, and/or -7 be substantially pure and/or sterile. When BMP-2, -4, -5, -6, and/or -7 is provided in a liquid solution, the liquid solution preferably is an aqueous solution, with a sterile aqueous solution being preferred. When BMP-2, -4, -5, -6, and/or -7 is provided as a dried form, reconstitution generally is by the addition of a suitable solvent. The solvent, e.g., sterile water or buffer, can optionally be provided in the kit.

The kit can include one or more containers for the composition containing BMP-2, -4, -5, -6, and/or -7. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of BMP-2, -4, -5, -6, and/or -7. For example, the kit can include a plurality of syringes, ampoules, foil packets, or blister packs, each containing a single unit dose of BMP-2, -4, -5, -6, and/or -7. The containers of the kits can be air tight and/or waterproof.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In one embodiment, the device is a syringe.

Generation of Variants: Production of Altered DNA and Peptide Sequences by Random Methods Amino acid sequence variants of BMP-2, -4, -5, -6, and/or -7 polypeptides or fragments thereof can be prepared by a number of techniques, such as random mutagenesis of DNA which encodes a BMP-2, -4, -5, -6, and/or -7 or a region thereof. Useful methods also include PCR mutagenesis and saturation mutagenesis. A library of random amino acid sequence variants can also be generated by the synthesis of a set of degenerate oligonucleotide sequences.

PCR Mutagenesis

In PCR mutagenesis, reduced Taq polymerase fidelity is used to introduce random mutations into a cloned fragment of DNA (Leung et al., 1989, *Technique* 1:11-15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., *Science* 229:242 (1985)). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, Tetrahedron 39:3 (1983); Itakura et al., in *Recombinant DNA, Proc. 3rd Cleveland Sympos. Macromolecules*, ed. AG Walton, Amsterdam:Elsevier, pp. 273-289 (1981); Itakura et al., Annu. Rev. Biochem. 53:323 (1984); Itakura et al., Science 198:1056 (1984); Ike et al., Nucleic Acid Res. 11:477 (1983). Such techniques have been employed in the directed evolution of other proteins (see, for example, Scott et al., Science 249:386-390 (1990); Roberts et al., Proc. Nat. Acad. Sci. USA 89:2429-2433 (1992); Devlin et al., Science 249: 404-406 (1990); Cwirla et al., Proc. Nat. Acad. Sci. USA 87: 6378-6382 (1990); as well as U.S. Pat. Nos. 5,223,409, 5,198, 346, and 5,096,815).

Generation of Variants: Production of Altered DNA and Peptide Sequences by Directed Mutagenesis Non-random or directed mutagenesis techniques can be used to provide specific sequences or mutations in specific regions. These techniques can be used to create variants that include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1-3.

Alanine Scanning Mutagenesis

Alanine scanning mutagenesis is a useful method for identification of certain residues or regions of the desired protein that are preferred locations or domains for mutagenesis, Cunningham and Wells (Science 244:1081-1085 (1989)). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (DNA 2:183 (1983)). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (Proc. Natl. Acad. Sci. USA 75: 5765 (1978)).

Cassette Mutagenesis

Another method for preparing variants, cassette mutagenesis, is based on the technique described by Wells et al. (Gene, 34:315 (1985)). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate variants. For example, the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening peptides, e.g., synthetic peptides, e.g., small molecular weight peptides (e.g., linear or cyclic peptides) or generated mutant gene products. Techniques for screening large gene libraries often include cloning the gene library into replicable expression vectors, transforming appropriate cells with the resulting library of vectors, and expressing the genes under conditions in which detection of a desired activity, assembly into a trimeric molecules, binding to natural ligands, e.g., a receptor or substrates, facilitates relatively easy isolation of the vector encoding the gene whose product was detected. Each of the techniques described below is amenable to high through-put analysis for screening large numbers of sequences created, e.g., by random mutagenesis techniques.

Two Hybrid Systems

Two hybrid (interaction trap) assays can be used to identify a protein that interacts with BMP-2, -4, -5, -6, and/or -7. These may include, e.g., agonists, superagonists, and antagonists of BMP-2, -4, -5, -6, and/or -7. (The subject protein and a protein it interacts with are used as the bait protein and fish proteins.). These assays rely on detecting the reconstitution of a functional transcriptional activator mediated by protein-protein interactions with a bait protein. In particular, these assays make use of chimeric genes which express hybrid proteins. The first hybrid comprises a DNA-binding domain fused to the bait protein. e.g., BMP-2, -4, -5, -6, and/or -7 or active fragments thereof. The second hybrid protein contains a transcriptional activation domain fused to a "fish" protein, e.g. an expression library. If the fish and bait proteins are able to interact, they bring into close proximity the DNA-binding and transcriptional activator domains. This proximity is sufficient to cause transcription of a reporter gene which is operably linked to a transcriptional regulatory site which is recognized by the DNA binding domain, and expression of the marker gene can be detected and used to score for the interaction of the bait protein with another protein.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al., Bio/Technology 9:1370-1371 (1991); and Goward et al., TIBS 18:136-140 (1992)). This technique was used in Sahu et al., J. Immunology 157:884-891 (1996), to isolate a complement inhibitor. In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phages M13, fd., and f1 are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al., J. Biol. Chem. 267:16007-16010 (1992); Griffiths et al., EMBO J. 12:725-734 (1993); Clackson et al., Nature 352:624-628 (1991); and Barbas et al., PNAS 89:4457-4461 (1992)).

A common approach uses the maltose receptor of *E. coli* (the outer membrane protein, LamB) as a peptide fusion partner (Charbit et al., EMBO 5:3029-3037 (1986)). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al., Vaccines 91:387-392 (1991)), PhoE (Agterberg, et al., Gene 88:37-45 (1990)), and PAL (Fuchs et al., Bio/Tech 9:1369-1372 (1991)), as well as large bacterial surface structures have served as vehicles for peptide display. Peptides can be fused to pilin, a protein which polymerizes to form the pilus-a conduit for interbacterial exchange of genetic information (Thiry et al., Appl. Environ. Microbiol. 55:984-993 (1989)). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al., Bio/Tech. 6, 1080-1083 (1988)). Surface proteins of other bacterial species have also served as peptide fusion partners. Examples include the *Staphylococcus* protein A and the outer membrane protease IgA of *Neisseria* (Hansson et al., J. Bacteriol. 174, 4239-4245 (1992) and Klauser et al., EMBO J. 9, 1991-1999 (1990)).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al., Proc. Nat. Acad. Sci. USA 89:1865-1869 (1992)). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al., Proc. Natl. Acad. Sci. U.S.A. 89:1869 (1992)).

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla et al., Proc. Natl. Acad. Sci. U.S.A. 87, 6378-6382 (1990)). A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al., J. Med. Chem. 37 (9):1233-1251 (1994)). These particular biases are not a factor in the LacI display system.

The number of small peptides available in recombinant random libraries is enormous. Libraries of $10^7$-$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3-6 orders of magnitude larger than the currently available phage/phagemid or plasmid libraries. Furthermore, the construction of the libraries, expression of the peptides, and screening, is done in an entirely cell-free format.

In one application of this method (Gallop et al., J. Med. Chem. 37 (9):1233-1251 (1994)), a molecular DNA library encoding $10^{12}$ decapeptides was constructed and the library expressed in an E. Coli S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. Anal. Biochem. 204: 357-364 (1992)). To identify the sequences of the active peptides one sequences the DNA produced by the phagemid host.

Secondary Screens for Inhibitors of the Alternative Pathway

The high through-put assays described above can be followed (or substituted) by secondary screens in order to identify biological activities which will, e.g., allow one skilled in the art to differentiate agonists from antagonists. The type of a secondary screen used will depend on the desired activity that needs to be tested. For example, an adipose tissue-related assay described herein can be used in which the ability to increase or mimic BMP-2, -4, -5, -6, and/or -7 activity in adipose tissue can be used to identify BMP-2, -4, -5, -6, and/or -7 agonists from a group of peptide fragments isolated though one of the primary screens described above.

Peptide Mimetics

The invention also provides for production of the protein binding domains of BMP-2, -4, -5, -6, and/or -7, to generate mimetics, e.g. peptide or non-peptide agents, e.g., agonists.

Non-hydrolyzable peptide analogs of critical residues can be generated using benzodiazepine (e.g., see Freidinger et al., in *Peptides: Chemistry and Biology*, G. R. Marshall ed., ESCOM Publisher: Leiden, Netherlands (1988)), azepine (e.g., see Huffman et al., in *Peptides: Chemistry and Biology*, G. R. Marshall ed., ESCOM Publisher: Leiden, Netherlands (1988)), substituted gamma lactam rings (Garvey et al., in *Peptides: Chemistry and Biology*, G. R. Marshall ed., ESCOM Publisher: Leiden, Netherlands (1988)), keto-methylene pseudopeptides (Ewenson et al., J. Med. Chem. 29:295 (1986); and Ewenson et al., in *Peptides: Structure and Function* (*Proceedings of the 9th American Peptide Symposium*), Pierce Chemical Co., Rockland, Ill. (1985)), b-turn dipeptide cores (Nagai et al., Tetrahedron Lett. 26:647 (1985); and Sato et al., J. Chem. Soc. Perkin Trans. 1:1231 (1986)), and b-aminoalcohols (Gordon et al., Biochem. Biophys. Res. Commun. 126:419-426 (1985); and Dann et al., Biochem. Biophys. Res. Commun. 134:71-77 (1986)).

EXAMPLES

Materials and Methods

Protocol for adipocyte differentiation

Preadipocytes were grown to confluence (day 0) in differentiation medium (Dulbecco's modified Earle's medium containing 10% Fetal Bovine Serum supplemented with 20 nM insulin and 1 nM T3). Adipocyte differentiation was induced by treating confluent cells for 48 hours in differentiation medium further supplemented with 0.5 mM isobutylmethylxanthine (IBMX), 0.5 mM dexamethazone, and 0.125 mM indomethacin. After this induction period (day 2), cells were placed back to differentiation medium, which was then changed every second day. After four more days in differentiation medium (day 6), cells (wildtype) exhibit a fully differentiated phenotype with massive accumulation of multilocular fat droplets.

Protocol for Lipid Staining

Dishes were washed twice with phosphate-buffered saline and fixed with 10% buffered formalin for at least 1 hour at room temperature. Cells were then stained for 2 hours at room temperature with a filtered oil red 0 solution (0.5% oil red O in isopropyl alcohol), washed twice with distilled water, and visualized.

Generation and Characterization of Brown Preadipocyte Cell Lines

Brown fat precursor cells were isolated from intrascapular brown fat of newborn mice and immortalized by SV40 T antigen. Preadipocytes showed a spindle-shaped morphology similar to fibroblasts. Following differentiation with an induction cocktail of 20 nM insulin, 1 nM thyroid hormone [3,5,3'-triiodothyronine (T3)], 0.5 µM dexamethazone, 0.125 mM indomethacin, and 0.5 mM isobutylmethylxanthine, preadipocytes became smaller, rounded up, accumulated fat, and the cytoplasm/nuclear-ratio increased dramatically. Once fully differentiated, multi-locular fat droplets could be detected both microscopically and by Oil Red-O staining. Expression of UCP-1 was detected at basal state and upon β-adrenergic stimulation, confirming the features of brown adipocytes (methods described in Klein et al., J. Biol. Chem. 274:34795-34802 (1999)).

Example 1

Characterization of Brown Preadipocyte Cell Lines: Differential Role of Insulin Receptor Substrates in Brown Adipogenesis and Thermogenesis Both insulin and IGF-1 have been shown to exert effects on adipocyte differentiation in vivo and in vitro (Gregoire et al., Physiol Rev 78:783-809 (1998); MacDougald et al., Trends Endocrinol. Metab. 13:5-11 (2002)). These factors utilize a complex signaling pathway to exert their pleiotropic biological effects involving activation of their respective cell surface receptors and phosphorylation of several intracellular insulin/IGF-1 receptor substrates (IRS). To determine the role of this signaling pathway in the regulation of brown adipogenesis and metabolism, brown preadipocyte cell lines were generated from wild-type (WT) and different IRS knockout (KO) mice (Fasshauer et al., Mol Cell Biol 21:319-329 (2001); Tseng et al., J. Biol. Chem. 277:31601-31611 (2002); Tseng et al., Mol Cell Biol 24:1918-1929 (2004)). These cells were studied in both their fibroblastic and differentiated states. As demonstrated by Oil Red O staining, WT and IRS-4 KO cells fully differentiated into mature adipocytes, with multi-locular fat droplets; IRS-2 KO cells exhibited a slight decrease in differentiation; IRS-3 KO cells show a moderate defect; and IRS-1 KO cells exhibit a severe defect in differentiation. This occurred not only at the levels of lipid accumulation, but also involved blockade of the normal pattern of progression in the transcriptional regulators of adipogenesis, such as C/EBPα and PPARγ, as well as thermogenic marker UCP-1.

These results demonstrate that the IRS signalling pathway plays a role in adipogenesis in these cells. The different IRS receptors participate to varying degrees, with IRS-1 having the most significant effect on differentiation.

Example 2

Existence of BMP Signaling Machinery in WT Brown Preadipocytes

BMPs initiate intracellular signaling by binding to cell surface receptors. Expression profiling data showed that all three forms of BMP receptors, RIa, RIb, and RII, were expressed in brown preadipocytes. BMP receptor type Ia (BMPRIa) is responsible for adipocyte differentiation, while type Ib receptor (BMPRIb) specified differentiation of osteoblasts (Chen et al., J. Cell. Biol. 142:295-305 (1998)). Consistent with these findings, BMPRIa was the dominant form of BMP receptor expressed in the brown preadipocyte cell lines. In addition, there was a 47% reduction in expression of BMPRIa in IRS-1 KO cells, which exhibited a severe defect in differentiation, suggesting that this receptor may play a role in differentiation of brown preadipocytes (FIG. 1). Transcripts of several BMPs were also expressed in these preadipocytes (data not shown), suggesting these differentiation modulators may act as autocrine/paracrine factors in regulation of brown adipogenesis.

Figure 2:
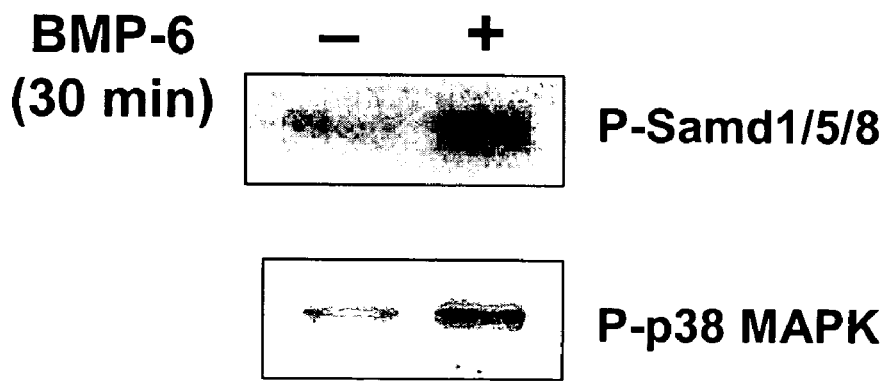
FIG. 2 is a Western blot showing activation of SMAD 1/5/8 and p38 MAPK in wild type preadipocytes after treatment with BMP6.

To see if BMPs were able to transmit signals into these cells, the WT brown preadipocytes were treated with recombinant BMP-6 (R&D Systems). BMP-6 quickly activated Smad 1/5/8 as monitored using a phospho-specific antibody (Cell Signaling) and p38 MAPK as monitored using a phospho-specific antibodies against p38 MAPK (Thr180/Tyr182) (Cell Signaling or Upstate Biotechnology) (FIG. 2).

Taken together, these data suggest that the brown preadipocytes possess functional components for BMP signaling, and these pathways may play a role in brown adipogenesis.

Example 3

Induction of Brown Adipocyte Differentiation by Bone Morphogenetic Proteins (BMPs) in the Absence of Induction Cocktail To begin to explore the role of BMPs on brown adipogenesis, the effect of six different BMPs on differentiation of WT brown preadipocytes was examined. In the absence of induction cocktail, 33 nM of BMPs were added to the normal culture medium and fresh medium was changed every 2 days. After 10 days of treatment with BMP-2, 4, 6, or 7, the cells showed a substantial increase in lipid accumulation as monitored by Oil Red O staining. BMP-5 exhibited a weaker effect relative to BMP-2, 4, 6, or 7, and BMP-3 had no effect on brown adipocyte differentiation. Similar results were observed in at least one other brown preadipocyte cell line derived from a different mouse with mixed genetic background. BMP-6 markedly induced the expression of PPARγ mRNA and protein during the course of differentiation.

In contrast, treatment with 33 nM BMP-6 for 8 days did not induce differentiation of white preadipocytes (3T3-L1 cells), demonstrating that the effect of BMP-6 is specific to brown preadipocytes.

The effect of BMP-6 and -7 on insulin- and insulin/T3-induced differentiation in the brown preadipocyte cell line and white preadipocytes (3T3-L1 cells) was also evaluated. The pro-differentiative effects shown by treatment of the brown preadipocytes with insulin, T3, BMP-6 or -7 alone, or insulin plus T3 alone, were strongly enhanced in the presence of a combination of BMP-6 or -7 plus insulin and T3 in the brown preadipocytes. Insulin plus B7, and to a lesser extent T3 plus B7, also produced strong combination effects. Little to no effect was seen in the 3T3-L1 cells.

Finally, the effect of BMP-6 on differentiation in the presence of induction cocktail was evaluated. As measured by Oil Red O staining, BMP-6 accelerated differentiation of wild-type brown adipocytes in the presence of induction cocktail, by approximately 1-2 days.

Example 4

Induction of PGC-1a and UCP-1 Expression by BMPs

Figure 3:
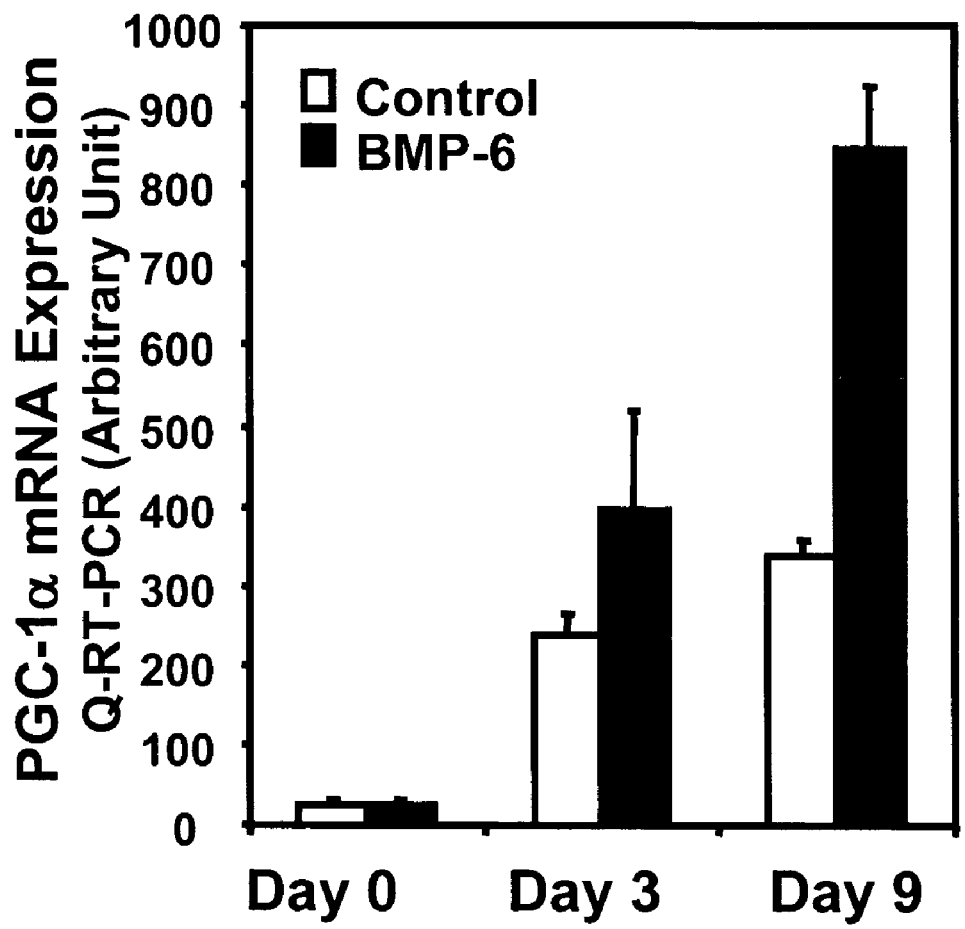
FIG. 3 is a bar graph showing an increase in PGC-1α mRNA expression as determined by quantitative RT-PCR at 0, 3, and 6 days after treatment with BMP-6.
Figure 4:
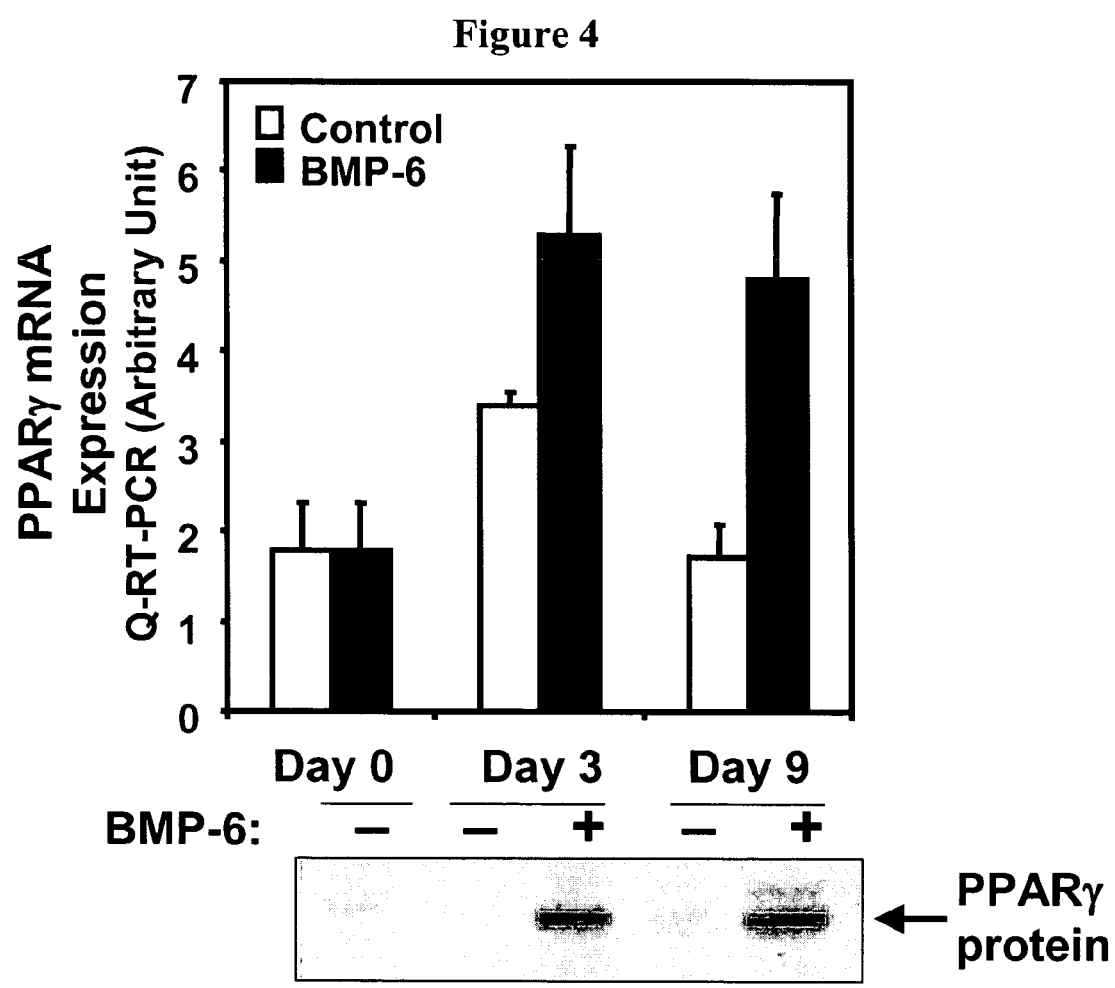
FIG. 4 is a bar graph showing an increase in PPARγ mRNA expression as determined by quantitative RT-PCR, and a Western blot showing an increase in PPARγ protein expression at 0, 3, and 6 days after treatment with BMP-6.

PGC-1α and UCP-1 are two decisive cellular markers of brown adipocytes. PPARγ is a nuclear hormone receptor that is a master transcription factor involved in white and brown adipocyte differentiation. To confirm that BMPs induced characteristics of brown adipocytes, PGC-1α mRNA and UCP-1 protein expression was examined by quantitative RT-PCR (Q-RT-PCR) and Western blot analysis, respectively, and PPARγ mRNA and protein expression was examined. Expression of PGC-1α mRNA was quickly induced by BMP-6 at day 3 and this was further increased as differentiation progressed to day 9 (FIG. 3). PPARγ mRNA and protein levels were approximately maximal by day 3 (FIG. 4).

Figure 5:
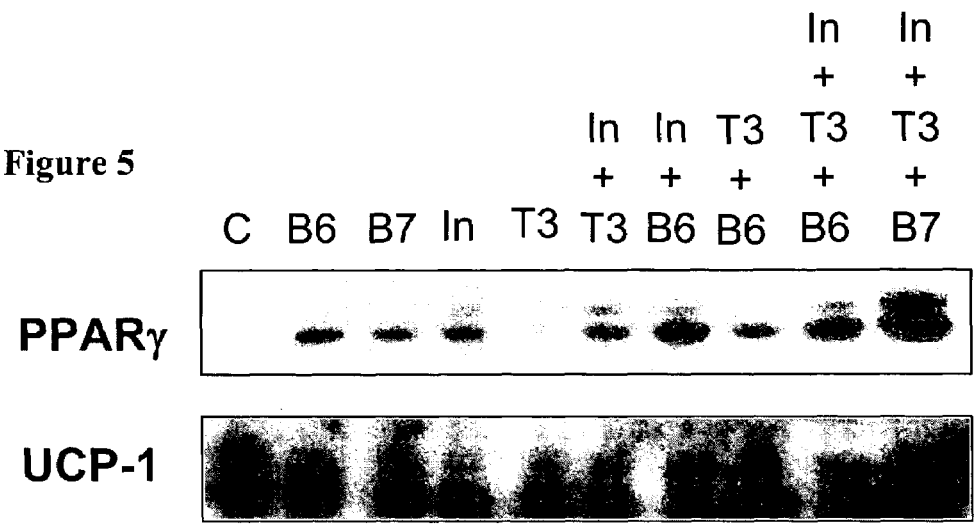
FIG. 5 is a Western blot showing the effect on PPARγ (top) and UCP 1 (bottom) expression of various combinations of BMP6 (B6), BMP7 (B7), insulin (In), and T3.

The effect of combination treatments on PPARγ and UCP-1 expression was further evaluated with various combinations of 1 nM T3, 20 nM insulin, 8.3 nM BMP-6, and/or 8.3 nM BMP-7. As shown in FIG. 5, the combination of Insulin (In), T3, and BMP-7 produced the strongest induction of both PPARγ and UCP-1 expression.

Figure 6:
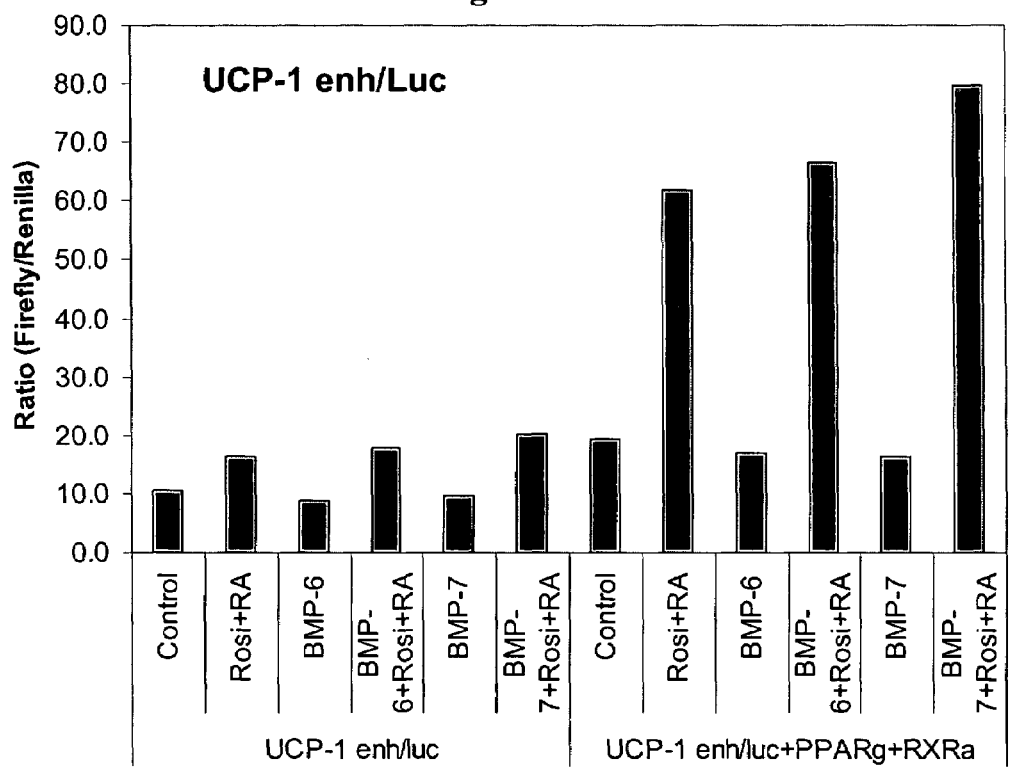
FIG. 6 is a bar graph showing the effect of BMP-6 and -7, and other compounds including 10 uM thiazolidinediones (TZD, sold under the brand name Rosiglitazone™, "Rosi", by GlaxosSmithKline) and retinoic acid (RA) on transcription from the UCP-1 promoter, in the presence and absence of PPARγ and the Retinoid X receptor, alpha (RxRa), using a UCP-1 expression reporter gene, with the UCP-1 promoter linked to the firefly luciferase gene.

Adaptive thermogenesis is an important component of energy homeostasis and a metabolic defense against obesity. PGC-1 increases the transcriptional activity of PPARγ and the UCP-1 promoter. Ectopic expression of PGC-1 in white adipose cells activates expression of UCP-1 and key mitochondrial enzymes of the respiratory chain, and increases the cellular content of mitochondrial DNA (Puigserver et al., Cell 92:829-839 (1998)). A UCP-1 expression reporter gene, with the UCP-1 promoter linked to the firefly luciferase gene (Id.), was used to evaluate the effect of BMPs and other compounds including 10 uM thiazolidinediones (TZD, sold under the brand name Rosiglitazone™, "Rosi", by GlaxoSmithKline) and retinoic acid (RA) on transcription from the UCP-1 promoter, in the presence and absence of PPARγ and the Retinoid X receptor, alpha (RxRa). As shown in FIG. 6, BMP-7 enhanced the TZD/RA-induced stimulation of promoter activity in the presence of PPARγ and RxRa.

These data indicate that BMPs may promote brown adipocyte differentiation via regulation of PGC-1α expression and modulate the thermogenic function of mature adipocytes by induction of UCP-1 protein expression.

Example 5

Effect of BMP-6 on Adipocyte Differentiation in WT and IRS-1 KO Brown Preadipocytes in the Presence of Induction Cocktail Recombinant human BMP-6 (R & D Systems, MN) was found to enhance differentiation of wildtype brown preadipocytes in the presence of standard conditions for induction of differentiation in vitro. The differentiation inductive effect of BMP-6 is more easily seen in brown adipocytes from IRS-1 knockout animals, which are known to have a defect in adipocyte differentiation. Thus, where almost no differentiation of BAT is seen under control conditions in IRS-1 knockouts, a substantial amount is seen when recombinant BMP-6 is added. BMP-6 can thus rescue, at least partially, the brown adipocyte differentiation defect in IRS-1 knockouts.

Using the standard assay for induction (W induction) of differentiation of preadipocytes, addition of exogenous recombinant human BMP-6 enhanced the level of differentiation from wildtype and IRS-1-knockout brown adipocytes and inhibited the level of differentiation of 3T3-L1 cells (a WAT cell line). In the absence of standard induction assay conditions (W/O induction), addition of exogenous recombinant human BMP-6 increased the level of brown adipocyte differentiation from wildtype mice. However, no change was seen either in BAT differentiation of preadipocytes from IRS-1 knockout mice or in WAT differentiation (3T3-L1). This indicates that BMP-6 alone has a positive effect on BAT differentiation in wildtype animals.

In addition, BMP-6 was found to cause changes in the morphology of wild-type brown pre-adipocytes. These changes are believed to correlate, at least in part, to induction of terminal differentiation.

Example 6

Involvement of BMP-6 in Adipocyte Differentiation

Figure 7:
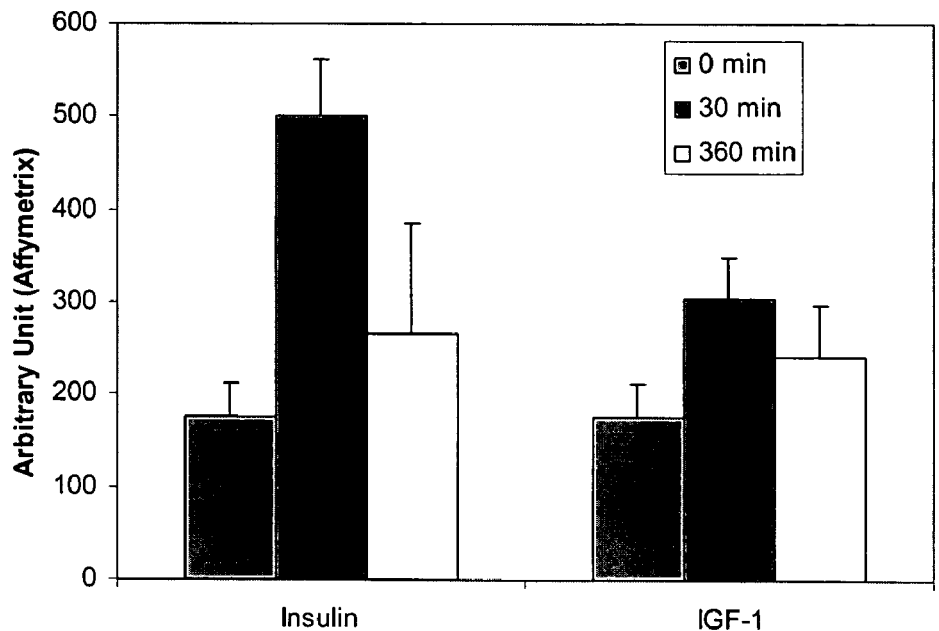
FIG. 7 is a bar graph illustrating the effect of insulin and IGF-1 (known inducers of adipocyte differentiation) on BMP-6 gene expression in wildtype brown adipocytes

Insulin and IGF-1 (known inducers of adipocyte differentiation) were found to acutely induce BMP-6 gene expression in wildtype brown adipocytes (FIG. 7). In turn, addition of recombinant BMP-6 induced expression of PPARγ and PGC-1 (a BAT-specific marker) during spontaneous differentiation. In addition, it was found that the time course of brown adipocyte differentiation correlates with the time course of appearance of mature BMP-6 segment, appearing at 2 days and increasing through 6 days post induction in wildtype cells.

Figure 8:
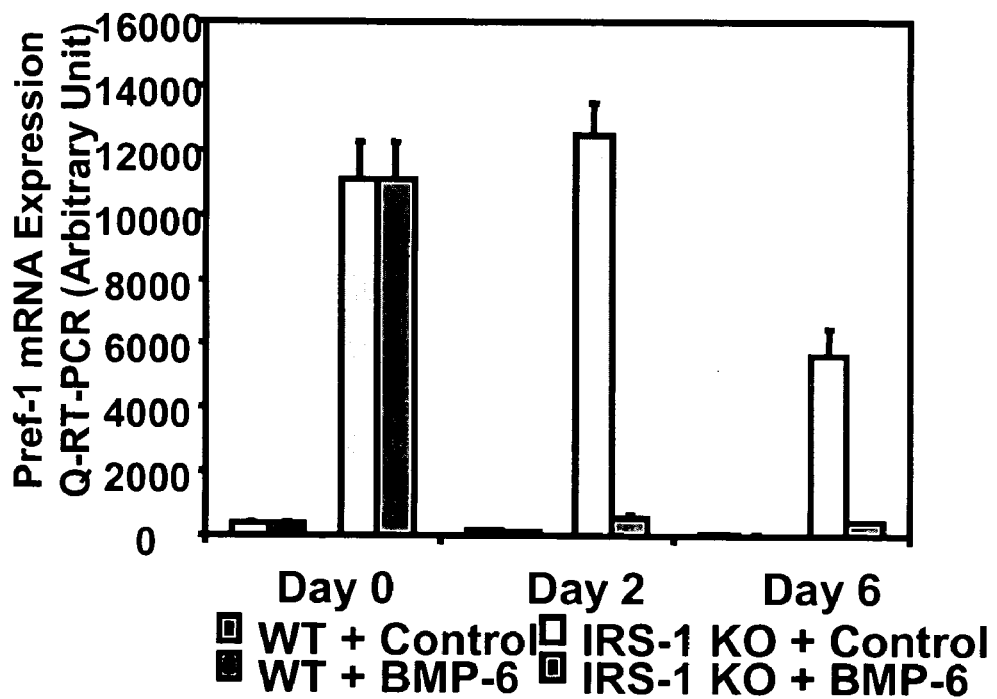
FIG. 8 is a bar graph illustrating the effect of treatment with 30 nM BMP-6 over six days on Pref-1 expression, as measured by quantitative RT-PCR.

As described above, cells brown preadipocytes from IRS-1 knockout animals are differentiation deficient. Pref-1 (preadipocyte factor-1) expression inhibits differentiation, and was found to be upregulated in the IRS-1 KO cells. Treatment with 30 nM BMP-6 over six days restores the defects in differentiation of IRS-1 KO brown preadipocytes, possibly by down-regulation of Pref-1 overexpression (FIG. 8). IRS-1 signalling plays an important role in insulin resistance, which is a hallmark of Type II diabetes. Thus, increasing BMP-6 activity in the insulin-sensitive cells may provide a treatment for insulin resistance.

Taken together, these data demonstrate the successful establishment of physiologically relevant brown preadipocyte cell lines and protocols to differentiate these cells in vitro. BMP signaling components are present in these brown preadipocytes. These data strongly suggest that BMPs may play a potential role in regulation of brown adipocyte differentiation and adaptive thermogenesis. At the molecular level, this is mediated, at least in part, by induction of PPARγ, PGC-1α, and UCP-1 expression.

Example 7

BMPs Induce Adipocyte Differentiation in Pluripotent Mouse Embryonic Fibroblasts To examine whether BMPs play a role in determining the fate of pluripotent stem cells toward brown adipocyte lineage, murine pluripotent cells, the effect of BMPs on adipogenesis was evaluated in mouse embryonic fibroblasts (MEFs), which were generated lab using the 3T3 protocol of Todaro and Green (J. Cell. Biol. 17:299-313 (1963)). The MEF cells were maintained in Dulbecco's Modified Eagle Medium (DMEM) supplemented with 10% FBS. To influence their differentiation toward the adipogenic direction, the MEFs were treated with TZD, a specific PPARγ ligand, or induced by the standard chemical/hormonal protocol as described herein.

MEF cells were grown in culture media containing 1 μM of rosiglitazone, BMPs, or a combination of both for 10 days. Oil Red O staining was performed at the end of differentiation to monitor the degree of adipogenesis. Treatment of C3H10T1/2 mesenchymal stem cells with TZD increases brown adipocyte differentiation and UCP-1 expression (Paulik et al., Cell Tissue Res. 290:79-87 (1997)). BMP-6 and BMP-7 both potentiated the TZD effects on adipocyte differentiation. Whole cell lysates were isolated from these cells to examine the expression of the adipogenic marker FAS (fatty acid synthase). The results indicated that the addition of BMP-6 or BMP-7 induced FAS protein expression in the presence of the induction cocktail or TZD.

All patents and references cited herein are hereby incorporated by reference in their entirety. It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A method of promoting brown adipocyte tissue (BAT) differentiation, the method comprising:
contacting a preadipocyte or adipocyte cell or tissue in vitro with a composition comprising a bone morphogenetic protein 7 (BMP-7) polypeptide, in an amount sufficient to promote BAT differentiation, thereby producing a differentiated cell or tissue; and
evaluating BAT differentiation in the differentiated cell or tissue by measuring uncoupling protein-1 expression, wherein an increase in uncoupling protein-1 expression indicates an increase in BAT differentiation.

2. The method of claim 1, wherein the cell or tissue comprises a brown preadipocyte.

3. The method of claim 1, wherein the cell or tissue comprises a white preadipocyte or white adipocyte.

4. The method of claim 1, wherein the cell or tissue is in culture.

5. The method of claim 4, wherein the cell or tissue is isolated from a living subject.

6. The method of claim 5, wherein the living subject is an obese human subject.

7. A method of decreasing fat stores or weight in a subject, the method comprising identifying a subject in need of decreasing fat stores or weight, and administering to the subject a therapeutically effective amount of a composition consisting essentially of a bone morphogenetic protein 7 (BMP-7) polypeptide.

8. The method of claim 1, where the BMP-7 polypeptide comprises amino acids 293-431 of SEQ ID NO:5.

9. The method of claim 7, where the BMP-7 polypeptide comprises amino acids 293-431 of SEQ ID NO:5.

10. The method of claim 1, wherein the level of BAT differentiation is further evaluated by measuring the level of a marker of BAT differentiation selected from the group consisting of PPAR-gamma Coactivator 1 (PGC-1), cytochrome oxidase activity, and mitochondrial DNA levels, wherein an increase in the level of the BAT marker indicates an increase in BAT differentiation.

11. The method of claim 1, wherein the level of BAT differentiation is further evaluated by measuring morphological changes specific to BAT.

12. The method of claim 1, further comprising implanting the differentiated cell in a subject.

13. The method of claim 12, wherein the subject is human.

14. A method for providing a cell culture enriched in brown adipocytes, the method comprising:
   providing a plurality of preadipocyte or adipocyte cells in vitro;
   contacting the plurality of cells with a composition comprising a bone morphogenetic protein 7 (BMP-7) polypeptide in an amount sufficient to promote BAT differentiation; and
   evaluating BAT differentiation in the culture, by measuring uncoupling protein-1 expression, wherein an increase in uncoupling protein-1 expression indicates an increase in BAT differentiation, thereby providing a culture enriched in brown adipocytes.

15. The method of claim 14, further comprising implanting at least one brown adipocyte from said enriched culture into a subject.

16. The method of claim 15, wherein the subject is human.

17. The method of claim 14, where the BMP-7 polypeptide comprises amino acids 293-431 of SEQ ID NO:5.

18. The method of claim 7, wherein the composition is administered intramuscularly.

19. The method of claim 7, wherein the composition is administered to a site of adipose tissue.

20. The method of claim 19, wherein the site of adipose tissue is a subcutaneous or omentum adipose pad.

21. The method of claim 19, where the BMP-7 polypeptide comprises amino acids 293-431 of SEQ ID NO:5.

* * * * *

UNITED STATES PATENT AND TRADEMARK OFFICE
CERTIFICATE OF CORRECTION

| | | |
|---|---|---|
| PATENT NO. | : 7,576,052 B2 | Page 1 of 1 |
| APPLICATION NO. | : 10/968791 | |
| DATED | : August 18, 2009 | |
| INVENTOR(S) | : Kahn et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 347 days Delete the phrase "by 347 days" and insert -- by 666 days --

Signed and Sealed this

Twenty-fourth Day of August, 2010

David J. Kappos
*Director of the United States Patent and Trademark Office*